(12) United States Patent  (10) Patent No.: US 9,236,024 B2
Coon  (45) Date of Patent: Jan. 12, 2016

(54) SYSTEMS AND METHODS FOR OBTAINING A PUPILLARY DISTANCE MEASUREMENT USING A MOBILE COMPUTING DEVICE

(71) Applicant: Glasses.com, Inc., Mason, OH (US)

(72) Inventor: Jonathan Coon, Austin, TX (US)

(73) Assignee: Glasses.com Inc., Mason, OH (US)

( * ) Notice: Subject to any disclaimer, the term of this patent is extended or adjusted under 35 U.S.C. 154(b) by 40 days.

(21) Appl. No.: 13/706,909

(22) Filed: Dec. 6, 2012

(65) Prior Publication Data

US 2013/0141468 A1   Jun. 6, 2013

Related U.S. Application Data

(60) Provisional application No. 61/567,475, filed on Dec. 6, 2011.

(51) Int. Cl.
| | | |
|---|---|---|
| G09G 5/00 | (2006.01) | |
| A61B 3/11 | (2006.01) | |
| G02C 13/00 | (2006.01) | |
| G06T 7/60 | (2006.01) | |
| G06Q 30/00 | (2012.01) | |

(52) U.S. Cl.
CPC *G09G 5/00* (2013.01); *A61B 3/111* (2013.01); *G02C 13/003* (2013.01); *G02C 13/005* (2013.01); *G06T 7/602* (2013.01); *G06Q 30/00* (2013.01); *G06T 2207/30201* (2013.01)

(58) Field of Classification Search
None
See application file for complete search history.

(56) References Cited

U.S. PATENT DOCUMENTS

| | | |
|---|---|---|
| 3,927,933 A | 12/1975 | Humphrey |
| 4,370,058 A | 1/1983 | Trötscher et al. |
| 4,467,349 A | 8/1984 | Maloomian |
| 4,522,474 A | 6/1985 | Slavin |
| 4,534,650 A | 8/1985 | Clerget et al. |
| 4,539,585 A | 9/1985 | Spackova et al. |
| 4,573,121 A | 2/1986 | Saigo et al. |
| 4,613,219 A | 9/1986 | Vogel |
| 4,698,564 A | 10/1987 | Slavin |
| 4,724,617 A | 2/1988 | Logan et al. |
| 4,730,260 A | 3/1988 | Mori et al. |
| 4,781,452 A | 11/1988 | Ace |

(Continued)

FOREIGN PATENT DOCUMENTS

| | | |
|---|---|---|
| DE | 10007705 A1 | 9/2001 |
| EP | 0092364 A1 | 10/1983 |

(Continued)

OTHER PUBLICATIONS

3D Morphable Model Face Animation, http://www.youtube.com/watch?v=nice6NYb_WA, Apr. 20, 2006.

(Continued)

*Primary Examiner* — Maurice L McDowell, Jr.
*Assistant Examiner* — Donna J Ricks
(74) *Attorney, Agent, or Firm* — Holland & Hart LLP

(57) ABSTRACT

A computer-implemented method for scaling an image is described. An image that depicts a device in contact with a user is obtained. The image depicts identifying information that is being displayed on a display of the device. A type of the device is identified based on the identifying information. A size of the device is determined based on the identified type of the device. At least a portion of the depiction of the user is scaled based on the determined size of the device.

20 Claims, 16 Drawing Sheets

(56) References Cited

U.S. PATENT DOCUMENTS

| | | |
|---|---|---|
| 4,786,160 A | 11/1988 | Fürter |
| 4,845,641 A | 7/1989 | Ninomiya et al. |
| 4,852,184 A | 7/1989 | Tamura et al. |
| 4,957,369 A | 9/1990 | Antonsson |
| 5,139,373 A | 8/1992 | Logan et al. |
| 5,255,352 A | 10/1993 | Falk |
| 5,257,198 A | 10/1993 | van Schoyck |
| 5,280,570 A | 1/1994 | Jordan |
| 5,281,957 A | 1/1994 | Schoolman |
| 5,428,448 A | 6/1995 | Albert-Garcia |
| 5,485,399 A | 1/1996 | Saigo et al. |
| 5,550,602 A | 8/1996 | Braeuning |
| 5,592,248 A | 1/1997 | Norton et al. |
| 5,631,718 A | 5/1997 | Markovitz et al. |
| 5,666,957 A | 9/1997 | Juto |
| 5,682,210 A | 10/1997 | Weirich |
| 5,720,649 A | 2/1998 | Gerber et al. |
| 5,724,522 A | 3/1998 | Kagami et al. |
| 5,774,129 A | 6/1998 | Poggio et al. |
| 5,809,580 A | 9/1998 | Arnette |
| 5,844,573 A | 12/1998 | Poggio et al. |
| 5,880,806 A | 3/1999 | Conway |
| 5,908,348 A | 6/1999 | Gottschald |
| 5,974,400 A | 10/1999 | Kagami et al. |
| 5,980,037 A | 11/1999 | Conway |
| 5,983,201 A | 11/1999 | Fay |
| 5,987,702 A | 11/1999 | Simioni |
| 5,988,862 A | 11/1999 | Kacyra et al. |
| D417,883 S | 12/1999 | Arnette |
| 6,016,150 A | 1/2000 | Lengyel et al. |
| 6,018,339 A | 1/2000 | Stevens |
| D420,037 S | 2/2000 | Conway |
| D420,379 S | 2/2000 | Conway |
| D420,380 S | 2/2000 | Simioni et al. |
| 6,024,444 A | 2/2000 | Little |
| D421,764 S | 3/2000 | Arnette |
| D422,011 S | 3/2000 | Conway |
| D422,014 S | 3/2000 | Simioni et al. |
| D423,034 S | 4/2000 | Arnette |
| D423,552 S | 4/2000 | Flanagan et al. |
| D423,553 S | 4/2000 | Brune |
| D423,554 S | 4/2000 | Conway |
| D423,556 S | 4/2000 | Conway |
| D423,557 S | 4/2000 | Conway |
| D424,094 S | 5/2000 | Conway |
| D424,095 S | 5/2000 | Brune et al. |
| D424,096 S | 5/2000 | Conway |
| D424,589 S | 5/2000 | Arnette |
| D424,598 S | 5/2000 | Simioni |
| D425,542 S | 5/2000 | Arnette |
| D425,543 S | 5/2000 | Brune |
| D426,568 S | 6/2000 | Conway |
| D427,225 S | 6/2000 | Arnette |
| D427,227 S | 6/2000 | Conway |
| 6,072,496 A | 6/2000 | Guenter et al. |
| 6,095,650 A | 8/2000 | Gao et al. |
| 6,102,539 A | 8/2000 | Tucker |
| D430,591 S | 9/2000 | Arnette |
| D432,156 S | 10/2000 | Conway et al. |
| D433,052 S | 10/2000 | Flanagan |
| 6,132,044 A | 10/2000 | Sternbergh |
| 6,139,141 A | 10/2000 | Zider |
| 6,139,143 A | 10/2000 | Brune et al. |
| 6,142,628 A | 11/2000 | Saigo |
| 6,144,388 A | 11/2000 | Bornstein |
| D434,788 S | 12/2000 | Conway |
| D439,269 S | 3/2001 | Conway |
| 6,208,347 B1 | 3/2001 | Migdal et al. |
| 6,222,621 B1 | 4/2001 | Taguchi et al. |
| 6,231,188 B1 | 5/2001 | Gao et al. |
| 6,233,049 B1 | 5/2001 | Kondo et al. |
| 6,246,468 B1 | 6/2001 | Dimsdale |
| 6,249,600 B1 | 6/2001 | Reed et al. |
| 6,281,903 B1 | 8/2001 | Martin et al. |
| 6,305,656 B1 | 10/2001 | Wemyss |
| 6,307,568 B1 | 10/2001 | Rom |
| 6,310,627 B1 | 10/2001 | Sakaguchi |
| 6,330,523 B1 | 12/2001 | Kacyra et al. |
| 6,356,271 B1 | 3/2002 | Reiter et al. |
| 6,377,281 B1 | 4/2002 | Rosenbluth et al. |
| 6,386,562 B1 | 5/2002 | Kuo |
| 6,415,051 B1 | 7/2002 | Callari et al. |
| 6,419,549 B2 | 7/2002 | Shirayanagi |
| 6,420,698 B1 | 7/2002 | Dimsdale |
| 6,434,278 B1 | 8/2002 | Hashimoto |
| 6,456,287 B1 | 9/2002 | Kamen et al. |
| 6,466,205 B2 | 10/2002 | Simpson et al. |
| 6,473,079 B1 | 10/2002 | Kacyra et al. |
| 6,492,986 B1 | 12/2002 | Metaxas et al. |
| 6,493,073 B2 | 12/2002 | Epstein |
| 6,508,553 B2 | 1/2003 | Gao et al. |
| 6,512,518 B2 | 1/2003 | Dimsdale |
| 6,512,993 B2 | 1/2003 | Kacyra et al. |
| 6,516,099 B1 | 2/2003 | Davison et al. |
| 6,518,963 B1 | 2/2003 | Waupotitsch et al. |
| 6,527,731 B2 | 3/2003 | Weiss et al. |
| 6,529,192 B1 | 3/2003 | Waupotitsch |
| 6,529,626 B1 | 3/2003 | Watanabe et al. |
| 6,529,627 B1 | 3/2003 | Callari et al. |
| 6,533,418 B1 | 3/2003 | Izumitani et al. |
| 6,535,223 B1 * | 3/2003 | Foley .................. 345/629 |
| 6,556,196 B1 | 4/2003 | Blanz et al. |
| 6,563,499 B1 | 5/2003 | Waupotitsch et al. |
| 6,583,792 B1 | 6/2003 | Agnew |
| 6,624,843 B2 | 9/2003 | Lennon |
| 6,634,754 B2 | 10/2003 | Fukuma et al. |
| 6,637,880 B1 | 10/2003 | Yamakaji et al. |
| 6,647,146 B1 | 11/2003 | Davison et al. |
| 6,650,324 B1 | 11/2003 | Junkins |
| 6,659,609 B2 | 12/2003 | Mothes |
| 6,661,433 B1 | 12/2003 | Lee |
| 6,664,956 B1 | 12/2003 | Erdem |
| 6,668,082 B1 | 12/2003 | Davison et al. |
| 6,671,538 B1 | 12/2003 | Ehnholm et al. |
| 6,677,946 B1 | 1/2004 | Ohba |
| 6,682,195 B2 | 1/2004 | Dreher |
| 6,692,127 B2 | 2/2004 | Abitbol et al. |
| 6,705,718 B2 | 3/2004 | Fossen |
| 6,726,463 B2 | 4/2004 | Foreman |
| 6,734,849 B2 | 5/2004 | Dimsdale et al. |
| 6,736,506 B2 | 5/2004 | Izumitani et al. |
| 6,760,488 B1 | 7/2004 | Moura et al. |
| 6,775,128 B2 | 8/2004 | Leitao |
| 6,785,585 B1 | 8/2004 | Gottschald |
| 6,791,584 B1 | 9/2004 | Xie |
| 6,792,401 B1 | 9/2004 | Nigro et al. |
| 6,807,290 B2 | 10/2004 | Liu et al. |
| 6,808,381 B2 | 10/2004 | Foreman et al. |
| 6,817,713 B2 | 11/2004 | Ueno |
| 6,825,838 B2 | 11/2004 | Smith et al. |
| 6,847,383 B2 | 1/2005 | Agnew |
| 6,847,462 B1 | 1/2005 | Kacyra et al. |
| 6,876,755 B1 | 4/2005 | Taylor et al. |
| 6,893,245 B2 | 5/2005 | Foreman et al. |
| 6,903,746 B2 | 6/2005 | Fukushima et al. |
| 6,907,310 B2 | 6/2005 | Gardner et al. |
| 6,922,494 B1 | 7/2005 | Fay |
| 6,943,789 B2 | 9/2005 | Perry et al. |
| 6,944,327 B1 | 9/2005 | Soatto |
| 6,950,804 B2 | 9/2005 | Strietzel |
| 6,961,439 B2 | 11/2005 | Ballas |
| 6,965,385 B2 | 11/2005 | Welk et al. |
| 6,965,846 B2 | 11/2005 | Krimmer |
| 6,968,075 B1 | 11/2005 | Chang |
| 6,980,690 B1 | 12/2005 | Taylor et al. |
| 6,999,073 B1 | 2/2006 | Zwern et al. |
| 7,003,515 B1 | 2/2006 | Glaser et al. |
| 7,016,824 B2 | 3/2006 | Waupotitsch et al. |
| 7,034,818 B2 | 4/2006 | Perry et al. |
| 7,043,059 B2 | 5/2006 | Cheatle et al. |
| 7,051,290 B2 | 5/2006 | Foreman et al. |
| 7,062,722 B1 | 6/2006 | Carlin et al. |
| 7,069,107 B2 | 6/2006 | Ueno |
| 7,095,878 B1 | 8/2006 | Taylor et al. |

(56) References Cited

U.S. PATENT DOCUMENTS

| | | | |
|---|---|---|---|
| 7,103,211 B1 | 9/2006 | Medioni et al. |
| 7,116,804 B2 | 10/2006 | Murase et al. |
| 7,133,048 B2 | 11/2006 | Brand |
| 7,152,976 B2 | 12/2006 | Fukuma et al. |
| 7,154,529 B2 | 12/2006 | Hoke et al. |
| 7,156,655 B2 | 1/2007 | Sachdeva et al. |
| 7,184,036 B2 | 2/2007 | Dimsdale et al. |
| 7,209,557 B2 | 4/2007 | Lahiri |
| 7,212,656 B2 | 5/2007 | Liu et al. |
| 7,212,664 B2 | 5/2007 | Lee et al. |
| 7,215,430 B2 | 5/2007 | Kacyra et al. |
| 7,218,150 B2 | 5/2007 | Kitagawa et al. |
| 7,218,323 B1 | 5/2007 | Halmshaw et al. |
| 7,219,995 B2 | 5/2007 | Ollendorf et al. |
| 7,224,357 B2 | 5/2007 | Chen et al. |
| 7,234,937 B2 | 6/2007 | Sachdeva et al. |
| 7,242,807 B2 | 7/2007 | Waupotitsch et al. |
| 7,290,201 B1 | 10/2007 | Edwards |
| 7,310,102 B2 | 12/2007 | Spicer |
| 7,324,110 B2 | 1/2008 | Edwards et al. |
| 7,415,152 B2 | 8/2008 | Jiang et al. |
| 7,421,097 B2 | 9/2008 | Hamza et al. |
| 7,426,292 B2 | 9/2008 | Moghaddam et al. |
| 7,434,931 B2 | 10/2008 | Warden et al. |
| 7,436,988 B2 | 10/2008 | Zhang et al. |
| 7,441,895 B2 | 10/2008 | Akiyama et al. |
| 7,450,737 B2 | 11/2008 | Ishikawa et al. |
| 7,489,768 B1 | 2/2009 | Strietzel |
| 7,492,364 B2 | 2/2009 | Devarajan et al. |
| 7,508,977 B2 | 3/2009 | Lyons et al. |
| 7,523,411 B2 | 4/2009 | Carlin |
| 7,530,690 B2 | 5/2009 | Divo et al. |
| 7,532,215 B2 | 5/2009 | Yoda et al. |
| 7,533,453 B2 | 5/2009 | Yancy |
| 7,540,611 B2 | 6/2009 | Welk et al. |
| 7,557,812 B2 | 7/2009 | Chou et al. |
| 7,563,975 B2 | 7/2009 | Leahy et al. |
| 7,573,475 B2 | 8/2009 | Sullivan et al. |
| 7,573,489 B2 | 8/2009 | Davidson et al. |
| 7,587,082 B1 | 9/2009 | Rudin et al. |
| 7,609,859 B2 | 10/2009 | Lee et al. |
| 7,630,580 B1 | 12/2009 | Repenning |
| 7,634,103 B2 | 12/2009 | Rubinstenn et al. |
| 7,643,685 B2 | 1/2010 | Miller |
| 7,646,909 B2 | 1/2010 | Jiang et al. |
| 7,651,221 B2 | 1/2010 | Krengel et al. |
| 7,656,402 B2 | 2/2010 | Abraham et al. |
| 7,657,083 B2 | 2/2010 | Parr et al. |
| 7,663,648 B1 | 2/2010 | Saldanha et al. |
| 7,665,843 B2 | 2/2010 | Xie |
| 7,689,043 B2 | 3/2010 | Austin et al. |
| 7,699,300 B2 | 4/2010 | Iguchi |
| 7,711,155 B1 | 5/2010 | Sharma et al. |
| 7,717,708 B2 | 5/2010 | Sachdeva et al. |
| 7,720,285 B2 | 5/2010 | Ishikawa et al. |
| D616,918 S | 6/2010 | Rohrbach |
| 7,736,147 B2 | 6/2010 | Kaza et al. |
| 7,755,619 B2 | 7/2010 | Wang et al. |
| 7,756,325 B2 | 7/2010 | Vetter et al. |
| 7,760,923 B2 | 7/2010 | Walker et al. |
| 7,768,528 B1 | 8/2010 | Edwards et al. |
| D623,216 S | 9/2010 | Rohrbach |
| 7,804,997 B2 | 9/2010 | Geng et al. |
| 7,814,436 B2 | 10/2010 | Schrag et al. |
| 7,830,384 B1 | 11/2010 | Edwards et al. |
| 7,835,565 B2 | 11/2010 | Cai et al. |
| 7,835,568 B2 | 11/2010 | Park et al. |
| 7,845,797 B2 | 12/2010 | Warden et al. |
| 7,848,548 B1 | 12/2010 | Moon et al. |
| 7,852,995 B2 | 12/2010 | Strietzel |
| 7,856,125 B2 | 12/2010 | Medioni et al. |
| 7,860,225 B2 | 12/2010 | Strietzel |
| 7,860,301 B2 | 12/2010 | Se et al. |
| 7,876,931 B2 | 1/2011 | Geng |
| 7,896,493 B2 | 3/2011 | Welk et al. |
| 7,907,774 B2 | 3/2011 | Parr et al. |
| 7,929,745 B2 | 4/2011 | Walker et al. |
| 7,929,775 B2 | 4/2011 | Hager et al. |
| 7,953,675 B2 | 5/2011 | Medioni et al. |
| 7,961,914 B1 | 6/2011 | Smith |
| 8,009,880 B2 | 8/2011 | Zhang et al. |
| 8,026,916 B2 | 9/2011 | Wen |
| 8,026,917 B1 | 9/2011 | Rogers et al. |
| 8,026,929 B2 | 9/2011 | Naimark |
| 8,031,909 B2 | 10/2011 | Se et al. |
| 8,031,933 B2 | 10/2011 | Se et al. |
| 8,059,917 B2 | 11/2011 | Dumas et al. |
| 8,064,685 B2 | 11/2011 | Solem et al. |
| 8,070,619 B2 | 12/2011 | Edwards |
| 8,073,196 B2 | 12/2011 | Yuan et al. |
| 8,090,160 B2 | 1/2012 | Kakadiaris et al. |
| 8,113,829 B2 | 2/2012 | Sachdeva et al. |
| 8,118,427 B2 | 2/2012 | Bonnin et al. |
| 8,126,242 B2 | 2/2012 | Brett et al. |
| 8,126,249 B2 | 2/2012 | Brett et al. |
| 8,126,261 B2 | 2/2012 | Medioni et al. |
| 8,130,225 B2 | 3/2012 | Sullivan et al. |
| 8,131,063 B2 | 3/2012 | Xiao et al. |
| 8,132,123 B2 | 3/2012 | Schrag et al. |
| 8,144,153 B1 | 3/2012 | Sullivan et al. |
| 8,145,545 B2 | 3/2012 | Rathod et al. |
| 8,155,411 B2 | 4/2012 | Hof et al. |
| 8,160,345 B2 | 4/2012 | Pavlovskaia et al. |
| 8,177,551 B2 | 5/2012 | Sachdeva et al. |
| 8,182,087 B2 | 5/2012 | Esser et al. |
| 8,194,072 B2 | 6/2012 | Jones et al. |
| 8,199,152 B2 | 6/2012 | Sullivan et al. |
| 8,200,502 B2 | 6/2012 | Wedwick |
| 8,204,299 B2 | 6/2012 | Arcas et al. |
| 8,204,301 B2 | 6/2012 | Xiao et al. |
| 8,204,334 B2 | 6/2012 | Bhagavathy et al. |
| 8,208,717 B2 | 6/2012 | Xiao et al. |
| 8,212,812 B2 | 7/2012 | Tsin et al. |
| 8,217,941 B2 | 7/2012 | Park et al. |
| 8,218,836 B2 | 7/2012 | Metaxas et al. |
| 8,224,039 B2 | 7/2012 | Ionita et al. |
| 8,243,065 B2 | 8/2012 | Kim |
| 8,248,417 B1 | 8/2012 | Clifton |
| 8,260,006 B1 | 9/2012 | Callari et al. |
| 8,260,038 B2 | 9/2012 | Xiao et al. |
| 8,260,039 B2 | 9/2012 | Shiell et al. |
| 8,264,504 B2 | 9/2012 | Naimark |
| 8,269,779 B2 | 9/2012 | Rogers et al. |
| 8,274,506 B1 | 9/2012 | Rees |
| 8,284,190 B2 | 10/2012 | Muktinutalapati et al. |
| 8,286,083 B2 | 10/2012 | Barrus et al. |
| 8,289,317 B2 | 10/2012 | Harvill |
| 8,290,769 B2 | 10/2012 | Taub et al. |
| 8,295,589 B2 | 10/2012 | Ofek et al. |
| 8,300,900 B2 | 10/2012 | Lai et al. |
| 8,303,113 B2 | 11/2012 | Esser et al. |
| 8,307,560 B2 | 11/2012 | Tulin |
| 8,330,801 B2 | 12/2012 | Wang et al. |
| 8,346,020 B2 | 1/2013 | Guntur |
| 8,355,079 B2 | 1/2013 | Zhang et al. |
| 8,372,319 B2 | 2/2013 | Liguori et al. |
| 8,374,422 B2 | 2/2013 | Roussel |
| 8,385,646 B2 | 2/2013 | Lang et al. |
| 8,391,547 B2 | 3/2013 | Huang et al. |
| 8,459,792 B2 | 6/2013 | Wilson |
| 8,605,942 B2 | 12/2013 | Takeuchi |
| 8,605,989 B2 | 12/2013 | Rudin et al. |
| 8,743,051 B1 * | 6/2014 | Moy et al. .................... 345/156 |
| 8,813,378 B2 | 8/2014 | Grove |
| 2001/0023413 A1 | 9/2001 | Fukuma et al. |
| 2001/0026272 A1 | 10/2001 | Feld et al. |
| 2001/0051517 A1 | 12/2001 | Strietzel |
| 2002/0010655 A1 | 1/2002 | Kjallstrom |
| 2002/0105530 A1 | 8/2002 | Waupotitsch et al. |
| 2002/0149585 A1 | 10/2002 | Kacyra et al. |
| 2003/0001835 A1 | 1/2003 | Dimsdale et al. |
| 2003/0030904 A1 | 2/2003 | Huang |
| 2003/0071810 A1 | 4/2003 | Shoov et al. |
| 2003/0110099 A1 | 6/2003 | Trajkovic et al. |

(56) References Cited

U.S. PATENT DOCUMENTS

| | | |
|---|---|---|
| 2003/0112240 A1 | 6/2003 | Cerny |
| 2004/0004633 A1* | 1/2004 | Perry et al. ............... 345/728 |
| 2004/0090438 A1 | 5/2004 | Alliez et al. |
| 2004/0217956 A1 | 11/2004 | Besl et al. |
| 2004/0223631 A1 | 11/2004 | Waupotitsch et al. |
| 2004/0257364 A1 | 12/2004 | Basler |
| 2005/0053275 A1 | 3/2005 | Stokes |
| 2005/0063582 A1 | 3/2005 | Park et al. |
| 2005/0111705 A1 | 5/2005 | Waupotitsch et al. |
| 2005/0128211 A1 | 6/2005 | Berger et al. |
| 2005/0162419 A1 | 7/2005 | Kim et al. |
| 2005/0190264 A1 | 9/2005 | Neal |
| 2005/0208457 A1 | 9/2005 | Fink et al. |
| 2005/0226509 A1 | 10/2005 | Maurer et al. |
| 2006/0012748 A1 | 1/2006 | Periasamy et al. |
| 2006/0017887 A1 | 1/2006 | Jacobson et al. |
| 2006/0067573 A1 | 3/2006 | Parr et al. |
| 2006/0127852 A1 | 6/2006 | Wen |
| 2006/0161474 A1 | 7/2006 | Diamond et al. |
| 2006/0212150 A1 | 9/2006 | Sims, Jr. |
| 2006/0216680 A1 | 9/2006 | Buckwalter et al. |
| 2007/0013873 A9 | 1/2007 | Jacobson et al. |
| 2007/0104360 A1 | 5/2007 | Huang et al. |
| 2007/0127848 A1 | 6/2007 | Kim et al. |
| 2007/0160306 A1 | 7/2007 | Ahn et al. |
| 2007/0183679 A1 | 8/2007 | Moroto et al. |
| 2007/0233311 A1 | 10/2007 | Okada et al. |
| 2007/0262988 A1 | 11/2007 | Christensen |
| 2008/0084414 A1 | 4/2008 | Rosel et al. |
| 2008/0112610 A1 | 5/2008 | Israelsen et al. |
| 2008/0136814 A1 | 6/2008 | Chu et al. |
| 2008/0152200 A1 | 6/2008 | Medioni et al. |
| 2008/0162695 A1 | 7/2008 | Muhn et al. |
| 2008/0163344 A1 | 7/2008 | Yang |
| 2008/0170077 A1 | 7/2008 | Sullivan et al. |
| 2008/0201641 A1 | 8/2008 | Xie |
| 2008/0219589 A1 | 9/2008 | Jung et al. |
| 2008/0240588 A1 | 10/2008 | Tsoupko-Sitnikov et al. |
| 2008/0246759 A1 | 10/2008 | Summers |
| 2008/0271078 A1 | 10/2008 | Gossweiler et al. |
| 2008/0278437 A1* | 11/2008 | Barrus et al. ............... 345/156 |
| 2008/0278633 A1 | 11/2008 | Tsoupko-Sitnikov et al. |
| 2008/0279478 A1 | 11/2008 | Tsoupko-Sitnikov et al. |
| 2008/0280247 A1 | 11/2008 | Sachdeva et al. |
| 2008/0294393 A1 | 11/2008 | Laake et al. |
| 2008/0297503 A1 | 12/2008 | Dickinson et al. |
| 2008/0310757 A1 | 12/2008 | Wolberg et al. |
| 2009/0010507 A1 | 1/2009 | Geng |
| 2009/0040216 A1 | 2/2009 | Ishiyama |
| 2009/0123037 A1 | 5/2009 | Ishida |
| 2009/0129402 A1 | 5/2009 | Moller et al. |
| 2009/0132371 A1 | 5/2009 | Strietzel et al. |
| 2009/0135176 A1 | 5/2009 | Snoddy et al. |
| 2009/0135177 A1 | 5/2009 | Strietzel et al. |
| 2009/0144173 A1 | 6/2009 | Mo et al. |
| 2009/0153552 A1 | 6/2009 | Fidaleo et al. |
| 2009/0153553 A1 | 6/2009 | Kim et al. |
| 2009/0153569 A1 | 6/2009 | Park et al. |
| 2009/0154794 A1 | 6/2009 | Kim et al. |
| 2009/0184960 A1 | 7/2009 | Carr et al. |
| 2009/0185763 A1* | 7/2009 | Park et al. ............... 382/311 |
| 2009/0219281 A1 | 9/2009 | Maillot |
| 2009/0279784 A1 | 11/2009 | Arcas et al. |
| 2009/0296984 A1 | 12/2009 | Nijim et al. |
| 2009/0304270 A1 | 12/2009 | Bhagavathy et al. |
| 2009/0310861 A1 | 12/2009 | Lang et al. |
| 2009/0316945 A1 | 12/2009 | Akansu |
| 2009/0316966 A1 | 12/2009 | Marshall et al. |
| 2009/0324030 A1 | 12/2009 | Frinking et al. |
| 2009/0324121 A1 | 12/2009 | Bhagavathy et al. |
| 2010/0030578 A1 | 2/2010 | Siddique et al. |
| 2010/0134487 A1 | 6/2010 | Lai et al. |
| 2010/0138025 A1 | 6/2010 | Morton et al. |
| 2010/0141893 A1 | 6/2010 | Altheimer et al. |
| 2010/0145489 A1 | 6/2010 | Esser et al. |
| 2010/0166978 A1 | 7/2010 | Nieminen |
| 2010/0179789 A1 | 7/2010 | Sachdeva et al. |
| 2010/0191504 A1 | 7/2010 | Esser et al. |
| 2010/0198817 A1 | 8/2010 | Esser et al. |
| 2010/0209005 A1 | 8/2010 | Rudin et al. |
| 2010/0277476 A1 | 11/2010 | Johansson et al. |
| 2010/0293192 A1 | 11/2010 | Suy et al. |
| 2010/0293251 A1 | 11/2010 | Suy et al. |
| 2010/0302275 A1 | 12/2010 | Saldanha et al. |
| 2010/0329568 A1 | 12/2010 | Gamliel et al. |
| 2011/0001791 A1 | 1/2011 | Kirshenboim et al. |
| 2011/0025827 A1 | 2/2011 | Shpunt et al. |
| 2011/0026606 A1 | 2/2011 | Bhagavathy et al. |
| 2011/0026607 A1 | 2/2011 | Bhagavathy et al. |
| 2011/0029561 A1 | 2/2011 | Slaney et al. |
| 2011/0040539 A1 | 2/2011 | Szymczyk et al. |
| 2011/0043540 A1 | 2/2011 | Fancher et al. |
| 2011/0043610 A1 | 2/2011 | Ren et al. |
| 2011/0071804 A1 | 3/2011 | Xie |
| 2011/0075916 A1 | 3/2011 | Knothe et al. |
| 2011/0096832 A1 | 4/2011 | Zhang et al. |
| 2011/0102553 A1 | 5/2011 | Corcoran et al. |
| 2011/0115786 A1 | 5/2011 | Mochizuki |
| 2011/0148858 A1 | 6/2011 | Ni et al. |
| 2011/0157229 A1 | 6/2011 | Ni et al. |
| 2011/0158394 A1 | 6/2011 | Strietzel |
| 2011/0166834 A1 | 7/2011 | Clara |
| 2011/0188780 A1 | 8/2011 | Wang et al. |
| 2011/0208493 A1 | 8/2011 | Altheimer et al. |
| 2011/0211816 A1 | 9/2011 | Goedeken et al. |
| 2011/0227923 A1 | 9/2011 | Mariani et al. |
| 2011/0227934 A1 | 9/2011 | Sharp |
| 2011/0229659 A1 | 9/2011 | Reynolds |
| 2011/0229660 A1 | 9/2011 | Reynolds |
| 2011/0234581 A1 | 9/2011 | Eikelis et al. |
| 2011/0234591 A1 | 9/2011 | Mishra et al. |
| 2011/0249136 A1 | 10/2011 | Levy |
| 2011/0262717 A1 | 10/2011 | Broen et al. |
| 2011/0267578 A1 | 11/2011 | Wilson |
| 2011/0279634 A1 | 11/2011 | Periyannan et al. |
| 2011/0292034 A1 | 12/2011 | Corazza et al. |
| 2011/0293247 A1 | 12/2011 | Bhagavathy et al. |
| 2011/0304912 A1 | 12/2011 | Broen et al. |
| 2011/0306417 A1 | 12/2011 | Sheblak et al. |
| 2012/0002161 A1 | 1/2012 | Altheimer et al. |
| 2012/0008090 A1 | 1/2012 | Atheimer et al. |
| 2012/0013608 A1 | 1/2012 | Ahn et al. |
| 2012/0016645 A1 | 1/2012 | Altheimer et al. |
| 2012/0021835 A1 | 1/2012 | Keller et al. |
| 2012/0038665 A1 | 2/2012 | Strietzel |
| 2012/0075296 A1 | 3/2012 | Wegbreit et al. |
| 2012/0079377 A1 | 3/2012 | Goosens |
| 2012/0082432 A1 | 4/2012 | Ackley et al. |
| 2012/0114184 A1 | 5/2012 | Barcons-Palau et al. |
| 2012/0114251 A1 | 5/2012 | Solem et al. |
| 2012/0121174 A1 | 5/2012 | Bhagavathy et al. |
| 2012/0130524 A1 | 5/2012 | Clara et al. |
| 2012/0133640 A1 | 5/2012 | Chin et al. |
| 2012/0133850 A1 | 5/2012 | Broen et al. |
| 2012/0147324 A1 | 6/2012 | Marin et al. |
| 2012/0158369 A1 | 6/2012 | Bachrach et al. |
| 2012/0162218 A1 | 6/2012 | Kim et al. |
| 2012/0166431 A1 | 6/2012 | Brewington et al. |
| 2012/0170821 A1 | 7/2012 | Zug et al. |
| 2012/0176380 A1 | 7/2012 | Wang et al. |
| 2012/0177283 A1 | 7/2012 | Wang et al. |
| 2012/0183202 A1 | 7/2012 | Wei et al. |
| 2012/0183204 A1 | 7/2012 | Aarts et al. |
| 2012/0183238 A1 | 7/2012 | Savvides et al. |
| 2012/0192401 A1 | 8/2012 | Pavlovskaia et al. |
| 2012/0206610 A1 | 8/2012 | Wang et al. |
| 2012/0219195 A1 | 8/2012 | Wu et al. |
| 2012/0224629 A1 | 9/2012 | Bhagavathy et al. |
| 2012/0229758 A1 | 9/2012 | Marin et al. |
| 2012/0256906 A1 | 10/2012 | Ross et al. |
| 2012/0263437 A1 | 10/2012 | Barcons-Palau et al. |
| 2012/0288015 A1 | 11/2012 | Zhang et al. |
| 2012/0294369 A1 | 11/2012 | Bhagavathy et al. |
| 2012/0294530 A1 | 11/2012 | Bhaskaranand |

(56) References Cited

U.S. PATENT DOCUMENTS

| | | |
|---|---|---|
| 2012/0299914 A1 | 11/2012 | Kilpatrick et al. |
| 2012/0306874 A1 | 12/2012 | Nguyen et al. |
| 2012/0307074 A1 | 12/2012 | Bhagavathy et al. |
| 2012/0314023 A1 | 12/2012 | Barcons-Palau et al. |
| 2012/0320153 A1 | 12/2012 | Barcons-Palau et al. |
| 2012/0321128 A1 | 12/2012 | Medioni et al. |
| 2012/0323581 A1 | 12/2012 | Strietzel et al. |
| 2013/0027657 A1 | 1/2013 | Esser et al. |
| 2013/0070973 A1 | 3/2013 | Saito et al. |
| 2013/0088490 A1 | 4/2013 | Rasmussen et al. |
| 2013/0187915 A1 | 7/2013 | Lee et al. |
| 2013/0201187 A1 | 8/2013 | Tong et al. |
| 2013/0271451 A1 | 10/2013 | Tong et al. |

FOREIGN PATENT DOCUMENTS

| | | | |
|---|---|---|---|
| EP | 0359596 A1 | 3/1990 | |
| EP | 0994336 A2 | 4/2000 | |
| EP | 1011006 A1 | 6/2000 | |
| EP | 1136869 A1 | 9/2001 | |
| EP | 1138253 A2 | 10/2001 | |
| EP | 0444902 B2 | 6/2002 | |
| EP | 1450201 A1 | 8/2004 | |
| EP | 1728467 A1 | 12/2006 | |
| EP | 1154302 B1 | 8/2009 | |
| FR | 2966038 A1 | 4/2012 | |
| GB | 2449885 A * | 10/2008 | ............... A61B 3/11 |
| GB | 2449855 A | 12/2008 | |
| JP | 2003345857 A | 12/2003 | |
| JP | 2004272530 | 9/2004 | |
| JP | 2005269022 | 9/2005 | |
| KR | 20000028583 | 5/2000 | |
| KR | 200000051217 | 8/2000 | |
| KR | 20040097200 | 11/2004 | |
| KR | 20080086945 | 9/2008 | |
| KR | 20100050052 | 5/2010 | |
| WO | WO 9300641 A1 | 1/1993 | |
| WO | WO 9604596 A1 | 2/1996 | |
| WO | WO 9740342 A2 | 10/1997 | |
| WO | WO 9740960 A1 | 11/1997 | |
| WO | WO 9813721 A1 | 4/1998 | |
| WO | WO 9827861 A1 | 7/1998 | |
| WO | WO 9827902 A2 | 7/1998 | |
| WO | WO 9835263 A1 | 8/1998 | |
| WO | WO 9852189 A2 | 11/1998 | |
| WO | WO 9857270 A1 | 12/1998 | |
| WO | WO 9956942 A1 | 11/1999 | |
| WO | WO 9964918 A1 | 12/1999 | |
| WO | WO 0000863 A1 | 1/2000 | |
| WO | WO 0016683 A1 | 3/2000 | |
| WO | WO 0045348 A1 | 8/2000 | |
| WO | WO 0049919 A1 | 8/2000 | |
| WO | WO 0062148 A1 | 10/2000 | |
| WO | WO 0064168 A1 | 10/2000 | |
| WO | WO 0123908 A1 | 4/2001 | |
| WO | WO 0132074 A1 | 5/2001 | |
| WO | WO 0135338 A1 | 5/2001 | |
| WO | WO 0161447 A1 | 8/2001 | |
| WO | WO 0167325 A1 | 9/2001 | |
| WO | WO 0174553 A2 | 10/2001 | |
| WO | WO 0178630 A1 | 10/2001 | |
| WO | WO 0188654 A2 | 11/2001 | |
| WO | WO 0207845 A1 | 1/2002 | |
| WO | WO 0241127 A2 | 5/2002 | |
| WO | WO 03079097 A1 | 9/2003 | |
| WO | WO 03084448 A1 | 10/2003 | |
| WO | WO 2007012261 A1 | 2/2007 | |
| WO | WO 2007017751 A1 | 2/2007 | |
| WO | WO 2007018017 A1 | 2/2007 | |
| WO | WO 2008009355 A1 | 1/2008 | |
| WO | WO 2008009423 A1 | 1/2008 | |
| WO | WO 2008135178 A1 | 11/2008 | |
| WO | WO 2009023012 A1 | 2/2009 | |
| WO | WO 2009043941 A1 | 4/2009 | |
| WO | 2010039976 | 4/2010 | |
| WO | 2010042990 | 4/2010 | |
| WO | WO 2011012743 A2 | 2/2011 | |
| WO | WO 2011095917 A1 | 8/2011 | |
| WO | WO 2011134611 A1 | 11/2011 | |
| WO | WO 2011147649 A1 | 12/2011 | |
| WO | WO 2012051654 A1 | 4/2012 | |
| WO | WO 2012054972 A1 | 5/2012 | |
| WO | WO 2012054983 A1 | 5/2012 | |

OTHER PUBLICATIONS

Visionix 3D iView, Human Body Measurement Newsletter, vol. 1., No. 2, Sep. 2005, pp. 2 and 3.
Blaise Aguera y Arcas demos Photosynth, May 2007. Ted.com, http://www.ted.com/talks/blaise_aguera_y_arcas_demos_photosynth.html.
ERC Tecnology Leads to Eyeglass "Virtual Try-on" System, Apr. 20, 2012, http://showcase.erc-assoc.org/accomplishments/microelectronic/imsc6-eyeglass.htm.
Information about Related Patents and Patent Applications, see the section below having the same title.
U.S. Appl. No. 13/775,785, filed Feb. 25, 2013, Systems and Methods for Adjusting a Virtual Try-On.
U.S. Appl. No. 13/775,764, filed Feb. 25, 2013, Systems and Methods for Feature Tracking.
U.S. Appl. No. 13/774,995, filed Feb. 22, 2013, Systems and Methods for Scaling a Three-Dimensional Model.
U.S. Appl. No. 13/774,985, filed Feb. 22, 2013, Systems and Methods for Generating a 3-D Model of a Virtual Try-On Product.
U.S. Appl. No. 13/774,983, filed Feb. 22, 2013, Systems and Methods for Generating a 3-D Model of a User for a Virtual Try-On Product.
U.S. Appl. No. 13/774,978, filed Feb. 22, 2013, Systems and Methods for Efficiently Processing Virtual 3-D Data.
U.S. Appl. No. 13/774,958, filed Feb. 22, 2013, Systems and Methods for Rendering Virtual Try-On Products.
U.S. Appl. No. 13/706,909, filed Dec. 6, 2012, Systems and Methods for Obtaining a Pupillary Distance Measurement Using a Mobile Computing Device.
PCT International Search Report for PCT International Patent Application No. PCT/US2012/068174, mailed Mar. 7, 2013.
PCT International Search Report for PCT International Patent Application No. PCT/US2013/042529, mailed Sep. 17, 2013.
PCT International Search Report for PCT International Patent Application No. PCT/US2013/042525, mailed Sep. 17, 2013.
PCT International Search Report for PCT International Patent Application No. PCT/US2012/042512, mailed Sep. 17, 2013.
PCT International Search Report for PCT International Patent Application No. PCT/US2012/042504, mailed Aug. 19, 2013.
PCT International Search Report for PCT International Patent Application No. PCT/US2012/042509, mailed Sep. 2, 2013.
PCT International Search Report for PCT International Patent Application No. PCT/US2012/042514, mailed Aug. 30, 2013.
PCT International Search Report for PCT International Patent Application No. PCT/US2012/042517, mailed Aug. 29, 2013.
PCT International Search Report for PCT International Patent Application No. PCT/US2013/042520, mailed Sep. 17, 2013.
Tracker, Tracker Help, Nov. 2009.
English Abstract and English Machine Translation of JP2004272530, Sep. 30, 2004.
English Abstract and English Machine Translation of KR20080086945, Sep. 29, 2008.
English Abstract and English Machine Translation of KR20100050052, May 13, 2010.
English Abstract and English Machine Translation of JP 2005269022, Sep. 29, 2005.
English Abstract of KR 20000028583, May 25, 2000.
English Abstract of KR 20000051217, Aug. 16, 2000.
Sinha et al., GPU-based Video Feautre Tracking and Matching, http::frahm.web.unc.edu/files/2014/01/GPU-based-Video-Feature-Tracking-And Matching.pdf, May 2006.
Dror et al., Recognition of Surface Relfectance Properties form a Single Image under Unknown Real-World Illumination, IEEE, Pro-

(56) References Cited

OTHER PUBLICATIONS ceedings of the IEEE Workshop on Identifying Objects Across Variations in Lighting: Psychophysics & Computation, Dec. 2011.
Simonite, 3-D Models Created by a Cell Phone, Mar. 23, 2011, url: http://www.technologyreview.com/news/423386/3-d-models-created-by-a-cell-phone/.

Fidaleo, Model-Assisted 3D Face Reconstruction from Video, AMFG'07 Analysis and Modeling of Faces and Gestures Lecture Notes in Computer Science vol. 4778, 2007, pp. 124-138.
Garcia-Mateos, Estimating 3D facial pose in video with just three points, CVPRW '08 Computer vision and Pattern Recognition Workshops, 2008.

* cited by examiner

SYSTEMS AND METHODS FOR OBTAINING A PUPILLARY DISTANCE MEASUREMENT USING A MOBILE COMPUTING DEVICE

RELATED APPLICATIONS

This application claims priority to U.S. Application No. 61/567,475, entitled SYSTEMS AND METHODS FOR OBTAINING A PUPILLARY DISTANCE MEASUREMENT USING A MOBILE COMPUTING DEVICE, and filed on Dec. 6, 2011, which is incorporated herein in its entirety by this reference.

BACKGROUND

Sales of prescription eyewear over the Internet have been limited in large part because users are unable to actually try on frames before purchasing. Systems are being developed to "virtually" try on different frames using a digital image of the user and digital images of the frames. The user typically uploads a digital image of the user's face. The user then selects different pairs of frames to "try on." Once the pair of frames is selected, an image of the selected frames is superimposed on the stored facial image. This combined image is then presented to the user so that the user can see his/her own image wearing the selected frames.

Another element in purchasing glasses over the Internet is preparation of the eyeglass lenses. The lenses are held spaced apart laterally with the frames. An important aspect of preparing eyeglass lenses is the pupillary distance, which is also referred to as inter-pupillary distance. This distance is the measurement from pupil to pupil and is required to properly prepare lenses for a particular set of frames.

Outside of Internet retail websites that sell glasses, the pupillary distance for the user is easily measured upon examining the user at any physical location where the user purchases glasses. In Internet-based sales, however, the Internet retail website must ask the user for his/her pupillary distance just as the website asks for the user's vision correction prescription. Since the pupillary distance measurement is not typically provided by eye care professionals as part of the user's prescription, it can be difficult for the user to understand and even obtain this measurement for submission at the website.

In many cases, users are intimidated with having to measure their own pupillary distance or with having to contact a physical retail site or their eye care professional in order to obtain this measurement. Opportunities exist for obtaining the pupillary distance measurement in ways outside of contacting a physical eyeglass retail site or eye care professional.

SUMMARY

A computer-implemented method for scaling an image is described. An image that depicts an unknown device in contact with a user is obtained. The image depicts identifying information that is being displayed on a display of the unknown device. A type of the device is identified based on the identifying information. A size or other feature of the device is determined based on the identified type of the device. At least a portion of the depiction of the user is scaled based on the determined size of the device. In some embodiments, a pupillary distance of the user may be determined based on the scaled depiction of the user.

In some embodiments, the image may be captured by the device itself. In some configurations, the identifying information may be provided in the form of a Quick Response (QR) code. The identifying information may include a make, a model, and/or a dimension of the device.

In one embodiment, a relationship between the depiction of the device and the depiction of the user may be determined. In some cases, scaling the at least a portion of the depiction of the user may include translating the scale of the previously unidentified device to the at least a portion of the depiction of the user based on the determined relationship.

In some configurations, the identifying information has a predetermined size. In one example, the depiction of the device or at least a portion of the depiction of the user may be scaled based on the predetermined size of the identifying information. In one embodiment, a distance between the device and a second device that is capturing the image may be determined based on the predetermined size of the identifying information. That determined distance between the displaying device and the capturing device can then, according to one embodiment, be used to scale the depiction of the user.

A device configured to scale an image is also described. The device may include a processor and memory in electronic communication with the processor. The memory may store instructions that are executable by the processor to obtain an image that depicts a device in contact with a user, the image depicting identifying information that is being displayed on a display of the device, identify a type of the device based on the identifying information, determine a size of the device based on the identified type of the device, and scale at least a portion of the depiction of the user based on the determined size of the device.

A computer-program product to scale an image is additionally described. The computer-program product includes non-transitory computer-readable medium having instructions thereon, the instructions being executable by a processor to obtain an image that depicts a device in contact with a user, the image depicting identifying information that is being displayed on a display of the device, identify a type of the device based on the identifying information, determine a size of the device based on the identified type of the device, and scale at least a portion of the depiction of the user based on the determined size of the device.

Features from any of the above-mentioned embodiments may be used in combination with one another in accordance with the general principles described herein. These and other embodiments, features, and advantages will be more fully understood upon reading the following detailed description in conjunction with the accompanying drawings and claims.

BRIEF DESCRIPTION OF THE DRAWINGS

The accompanying drawings illustrate a number of exemplary embodiments and are a part of the specification. Together with the following description, these drawings demonstrate and explain various principles of the instant disclosure.

Figure 1:
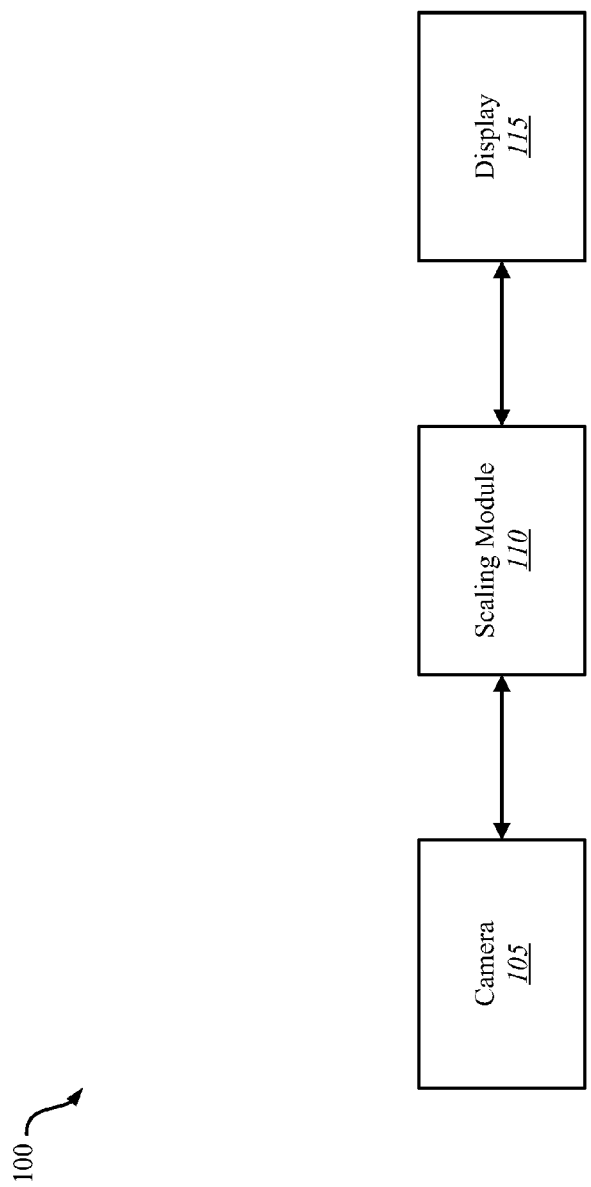
FIG. 1 illustrates an example system in accordance with the present disclosure for use in determining a pupillary distance.

While the embodiments described herein are susceptible to various modifications and alternative forms, specific embodiments have been shown by way of example in the drawings and will be described in detail herein. However, the exemplary embodiments described herein are not intended to be limited to the particular forms disclosed. Rather, the instant disclosure covers all modifications, equivalents, and alternatives falling within the scope of the appended claims.

DETAILED DESCRIPTION OF EXEMPLARY EMBODIMENTS

One aspect of the present disclosure relates to obtaining a pupillary distance using a handheld mobile device, such as, for example, an iPhone™, iPod™ iPad™, PDA, tablet, laptop, or smart phone. In one embodiment, the handheld mobile device is used to take a picture of the user with the handheld mobile device in the picture. One way to take this picture is to have the user stand in front of a mirror with the handheld mobile device positioned at a predetermined location relative to the user's face (e.g., contacting the user's chin) and the handheld mobile device takes a picture of the image in the mirror. The handheld mobile device or other computing device may scale the picture taken by the handheld mobile device based on, for example, the dimensions of the handheld mobile device or a portion thereof, or identifying information displayed on a display of the handheld device that appears in the picture.

The identifying information displayed by the handheld mobile device may include, for example, information that identifies a make, model, or other identifier of the handheld mobile device itself. Other identifying information may include, for example, dimensions of the screen of the handheld mobile device. Other identifying information may include, for example, symbols, codes, color schemes, patterns, or other information related to the handheld mobile device that would identify or lead to identification of a dimension of the handheld mobile device that is displayed in the picture for purposes of scaling the image in the picture and determining the user's pupillary distance.

Another aspect of the present disclosure relates to using information displayed by the mobile device as an identifier for the handheld mobile device, wherein the identifying information is displayed in a picture taken by a camera separate and remote from the handheld mobile device. In one example, the camera is connected to a computing device. The camera collects an image of the handheld mobile device positioned a predetermined position relative to a user's face (e.g., in contact with the user's chin or just below the user's nose). The computing device identifies the handheld mobile device and its features based on the information displayed on the screen of the handheld mobile device, which is captured by the camera. Based on the identification of the handheld mobile device, the computing device may use one or more features of the handheld mobile device to scale the image of the user and handheld mobile device collected by the camera and compute the user's pupillary distance.

According to yet another exemplary embodiment, a distance between the handheld mobile device and a second device that is capturing the image may be determined based on the size and information associated with the identifying information. That determined distance between the displaying device and the capturing device can then, according to one embodiment, be used to scale the depiction of the user.

In the embodiments described above, once the image has been scaled, either by the handheld mobile device, a separate computing device, or other device (e.g., a device accessible through a communications network), the user's pupillary distance may be determined using the scale. The user may then use the determined pupillary distance to order a pair of glasses over the Internet, other communications network, or other resource besides an eye care professional.

Referring now to the Figures, FIG. 1 illustrates an example system 100 in accordance with the present disclosure for use in determining a pupillary distance. The system 100 includes a camera 105, a scaling module 110, and a display 115. The camera 105 may be used to collect an image of a user and a handheld mobile device positioned at a predetermined location relative to the user's face (e.g., in contact with the user's chin or forehead). The display 115 may be part of the handheld mobile device. The display 115 may display identifying information about the handheld mobile device that is captured in a picture taken by camera 105. In other examples, the display 115 may provide a picture window that is visible by the user to confirm that the user and the handheld mobile device are properly positioned within the picture capturing window before taking a picture.

The scaling module 110 may operate to analyze the image collected by the camera 105 and determine a scale of the image based on, at least in part, either the handheld mobile device or the identifying information displayed on the display 115 of the handheld mobile device. Once the scale of the image is determined using the scaling module 110, a pupillary distance of the user shown in the image may be determined and presented to the user or a third party.

In some embodiments, the system 100 is a handheld mobile device that includes the camera 105, scaling module 110, and display 115. In other arrangements, the system 100 includes a camera 105 that is separate and/or remote from the handheld mobile device. The system 100 may include the scaling module 110 being carried by and/or operated by a separate computing device from the handheld mobile device.

Figure 2:
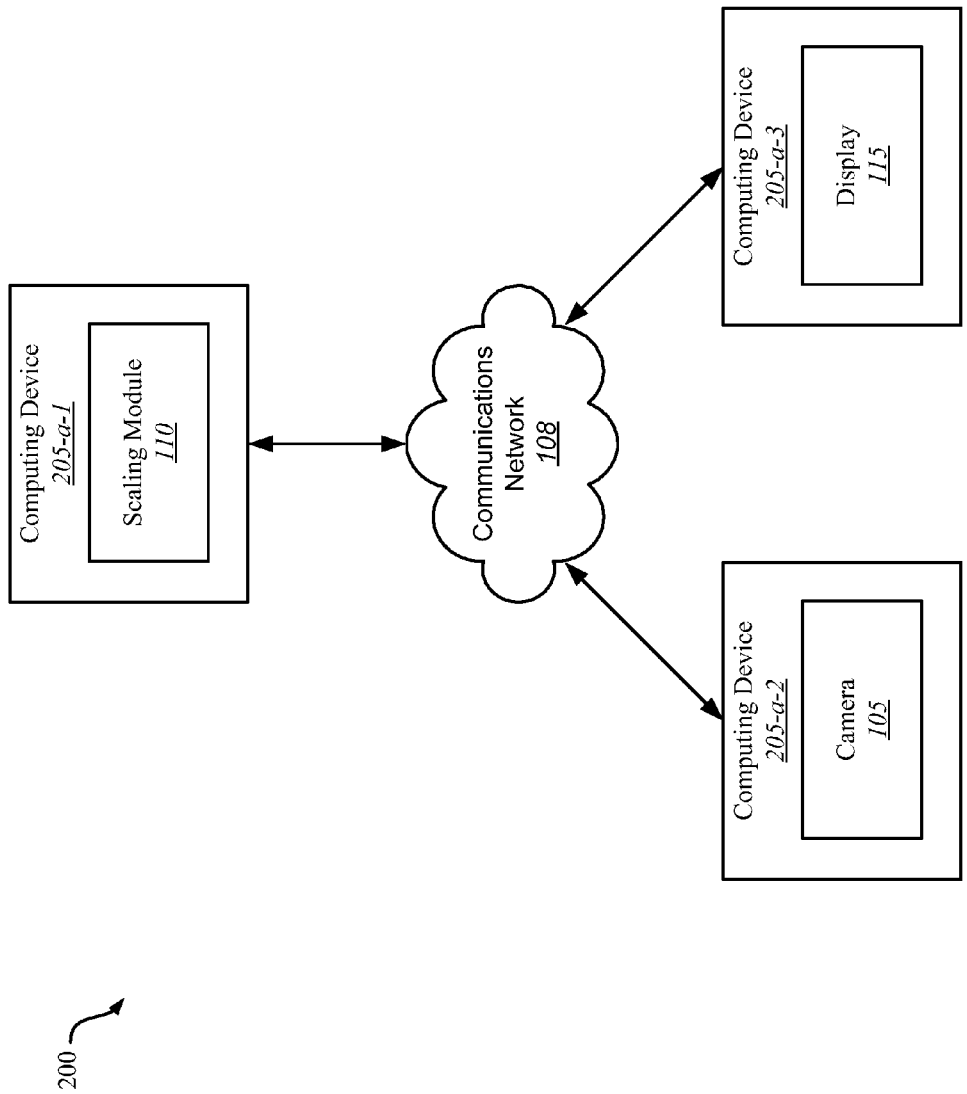
FIG. 2 is a block diagram illustrating another example of a system in which the present systems and methods may be implemented.

FIG. 2 is a block diagram illustrating another example of a system 200 in which the present systems and methods may be implemented. In one example, the system 200 may include a first computing device 205-*a*-1 that includes the scaling module 110, a second computing device 205-*a*-2 that includes the camera 105, and a third computing device 205-*a*-3 that includes the display 115. In some embodiments, each computing device 205 may communicate with another computing device 205 via the communications network 108. In one example, the communications network 108 may be the Internet.

In one embodiment, each of the computing devices 205-*a* (1-3) may be separate computing devices 205. For example, the first computing device 205-*a*-1 may be a cloud based server, the second computing device 205-*a*-2 may be a webcam attached to a computer, and the third computing device 205-*a*-3 may be a mobile device. In this example, the second computing device 205-*a*-2 may capture an image of a user holding the third computing device 205-*a*-3 in contact with the user's face along with the device specific information that is displayed on the display 115 of the third computing device 205-*a*-3. In this example, the second computing device 205-*a*-2 may communicate the image to the scaling module 110 on the first computing device 205-*a*-1 via the communications network 108. In one example, the scaling module 110 may determine the pupillary distance of the user's pupils by scaling the depiction of the user based on the known size of the third computing device 205-*a*-3 (as identified by the QR code displayed on the display 115, for example). The user may then use the pupillary distance measurement for purposes of, for example, obtaining a pair of eyeglasses using an Internet-based retail website.

In another example, two or more of the computing devices 205 may be the same computing device 205. For example, the second computing device 205-*a*-2 and the third computing device 205-*a*-3 may be embodied in a single computing device 205. In another example, the first computing device 205-*a*-1 and the second computing device 205-*a*-2 may be the same computing device 205. In yet another example, the first computing device 205-*a*-1, the second computing device 205-*a*-2, and the third computing device 205-*a*-3 may each be in a single computing device 205. In some cases, the computing device 205 may include both the camera 105 and the display 115. Thus, in some exemplary embodiments, the computing device that is capturing the image may be the same device that is being used to scale the depiction of the user.

Figure 3:
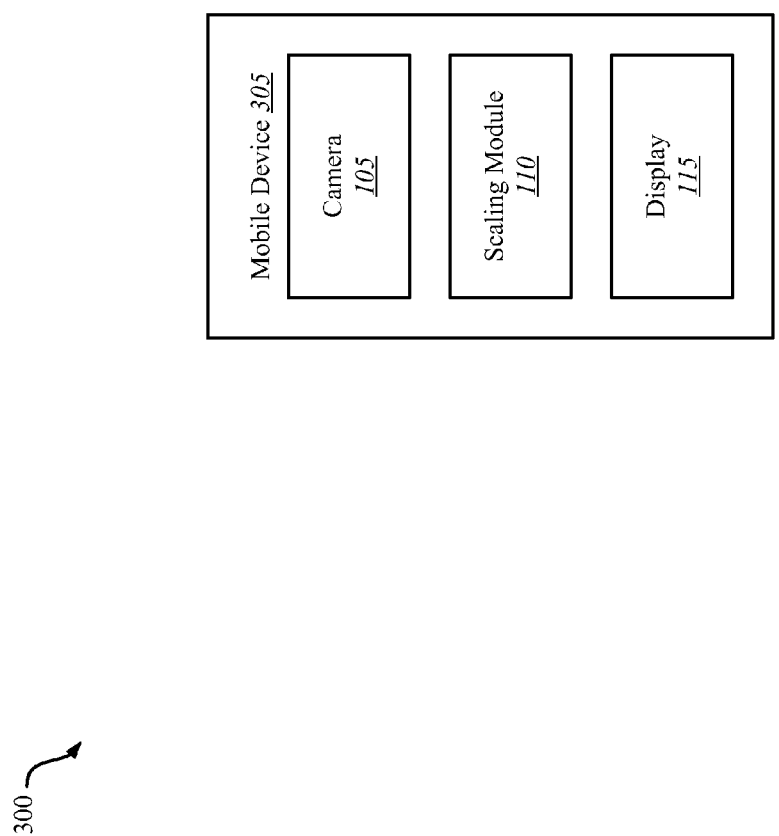
FIG. 3 illustrates a mobile device that includes the camera, the scaling module, and the display.

For instance, FIG. 3 illustrates a mobile device 305 that includes the camera 105, the scaling module 110, and the display 115. Examples of mobile devices include cellular phones, smart phones, tablets, PDAs, cameras, and the like. In one example, the mobile device 305 may use the camera 105 to capture an image of a reflection of a user holding the mobile device 305 to the user's face along with the any information displayed on the display 115. The scaling module 110 may then be used to scale the captured image and/or determine a pupillary distance of the user.

In some configurations, the computing device that includes the display 115 (the mobile device 305 and/or the third computing device 205-*a*-3, for example) may access a website via the Internet (e.g., communications network 108). In some cases, the type of computing device may be determined by the scaling module 110 based on device specific information or displays collected from the browser session created when the website is accessed. In some configurations, the website may cause an application (e.g., a browser) to display (via the display 115, for example) device specific information or indicators based on the type of device that is accessing the website. For example, the website may cause the application to display a code, such as first Quick Response (QR) code, when the computing device is an iPhone 4s, a second QR code when the computing device is an iPhone 5, and a third QR code when the computing device is a SAMSUNG GALAXY III. In some configurations, the displayed information (e.g., device specific QR code) may be formatted specifically for the display 115 of the computing device that it is being displayed on. For instance, that information may be precisely formatted based on the screen size and number of pixels in the display 115 of the computing device. In some cases, this may allow the QR code itself to be a scaling marker.

In some cases, information collected from the camera 105 and output from the scaling module 110 may be uploaded to a database, server, or processor via the communications network 108. Alternatively, the information may be uploaded to a provider of prescription eyewear. In some examples, the computing device 205 and mobile device 305 may be in communication via the communications network 108.

Figure 4:
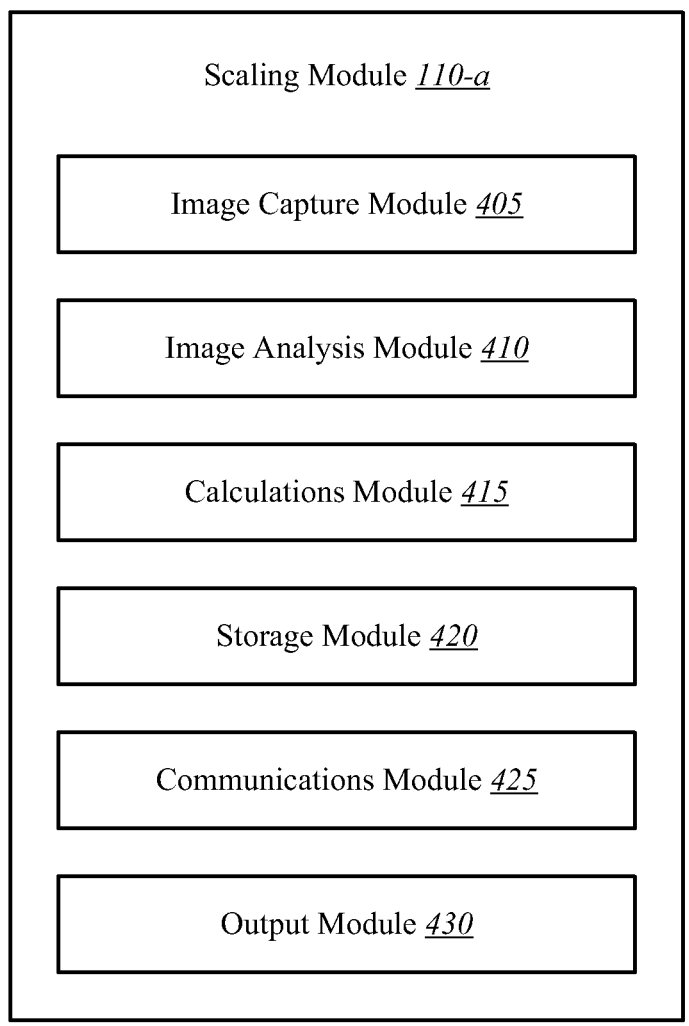
FIG. 4 is a block diagram illustrating an example of a scaling module.

FIG. 4 is a block diagram illustrating an example 400 of a scaling module 110-*a*. The scaling module 110-*a* may be an example of the scaling module 110 illustrated in FIGS. 1, 2, and/or 3. In some configurations, the scaling module 110-*a* may include an image capture module 405, and image analysis module 410, a calculations module 415, a storage module 420, a communications module 425, and an output module 430.

In one embodiment, the image capture module 405 may interface with the camera 105 to capture an image. For example, the image capture module 405 may interface with the camera 105 to capture an image of a user holding a mobile device in contact with the user's face. In one example, the image may capture the information that is displayed by the display 115 of the mobile device. In another embodiment, the image capture module 405 may obtain an image that was previously captured (that depicts the mobile device in contact with the user's face along with any information being displayed on the display 115 of the mobile device).

In one embodiment, the image analysis module 410 may analyze the image received from the camera 105. For example, the image analysis module 410 may identify, for example, pupils of the user, dimensions of the handheld mobile device, and information displayed on a display of the handheld mobile device.

In one embodiment, the calculations module 415 may be used to calculate, for example, a scale of an image delivered to scaling module 110 from camera 105. In some configurations, the calculations module 415 may also operate to determine a pupillary distance of a user included in the image.

In one embodiment, the storage module 420 may store images and other data that is to be communicated to or from the scaling module 110 via, for example, the communications module 425. In some embodiments, the storage module 420 may hold images or other data used by the image analysis module 410 and/or the calculations module 415. In some configurations, the communications module 425 may operate to provide communication between the scaling module 110, camera 105, computing device 205, and/or mobile device 305, either directly or via, for example, communications network 108.

Figure 5:
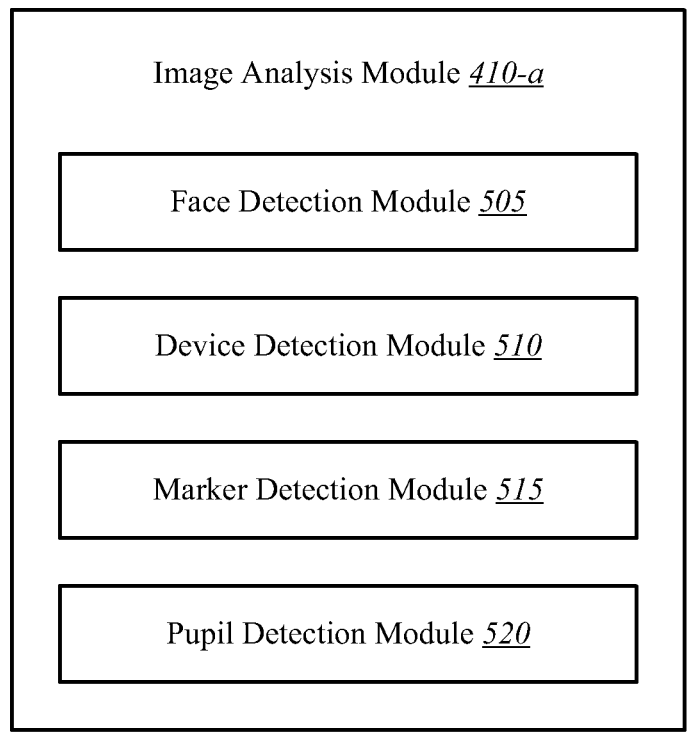
FIG. 5 is a block diagram illustrating one example of an image analysis module.

FIG. 5 is a block diagram illustrating one example 500 of an image analysis module 410-*a*. The image analysis module 410-*a* may be one example of the image analysis module 410 illustrated in FIG. 4. In some configurations, the image analysis module 410-*a* may include a face detection module 505, a device detection module 510, a marker detection module 515, and a pupil detection module 520.

In one embodiment, the face detection module 505 may detect various parts of a user's face. For example, the face detection module 505 may detect the forehead, eyes, nose, cheeks, lips, and/or chin, etc. of the user. In some configurations, the face detection module 505 may detect which portion of the user's face is in contact with the device. For instance, the face detection module 505 may detect that the device is touching the user's chin.

In one embodiment, the device detection module 510 may detect dimensions of the device relative to the user's face. For example, the device detection module 510 may detect the relationship between some measurement (the pupillary distance, for example) of the user's face and the dimensions of the device. It may be noted, however, that the actual dimensions of the device may be unknown until the marker is displayed and the type of the device is known. In some embodiments, the device detection module 510 may detect the type of device that is being held up to the user's face. For example, the device detection module 510 may detect the type of device based one or more markers on the device itself and/or a marker (e.g., information) displayed on the display 115 of the device.

In one embodiment, the marker detection module 515 may detect one or more markers (that provide information about the make and model of the device, for example) that are captured in the image. For example, the marker detection module 515 may detect a marker that was displayed on the display 115 of the device when the image was captured. For instance, the marker detection module 515 may detect a QR code indicating the type of device (make and model of the device, for example) that is touching the user's face. In some embodiments, the marker detection module 515 may identify one or markers and determine a type of device based on the identified marker. For instance, the marker detection module 520 may identify that a QR code displayed on the display 115 of a device corresponds to the QR code for an iPhone 5. In this example, the marker detection module 515 and/or the device detection module 510 may detect that the device is an iPhone 5 based on the detected marking.

In one embodiment, the pupil detection module 520 may detect the pupils of the user. For example, the pupil detection module 520 may detect the center of the pupil using the pupil itself and/or one or more attributes of the user's eye (e.g., the iris).

Figure 6:
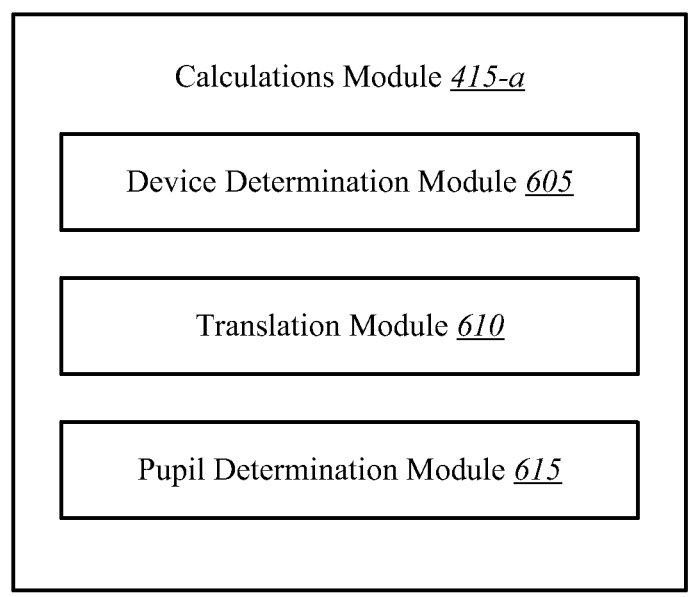
FIG. 6 is a block diagram illustrating one example of a calculations module.

FIG. 6 is a block diagram illustrating one example 600 of a calculations module 415-*a*. The calculations module 415-*a* may be an example of the calculations module 415 illustrated in FIG. 4. In some configurations, the calculations module 415-*a* may include a device determination module 605, a translation module 610, and a pupil determination module 615.

In one embodiment, the device determination module 605 may determine the physical dimensions of the device in the image based on the identified device type (identified using the device detection module 510 and/or the marker detection module 515, for example). In some embodiments, the device determination module 605 may scale one or more other portions of the image based on the known size of the device. For example, the device determination module 605 may scale the face of the user using the known dimensions of the depicted device.

In some cases, the translation module 610 may translate the way that the known dimensions of the device are used to scale the user's face to compensate for differences in depth between various portions of the face. For example, if the device is touching the chin of the user then the scaling of the image in the eye area may be adjusted to account for the difference in depth between the user's chin and the user's eyes. For instance, an average distance between the average chin and the average eyes may be used to account for the differences in depth for the user's face.

In one embodiment, the pupil determination module 615 may determine the pupillary distance between the pupils of the user. For example, the distance between the pupils in the scaled image may be used to determine the pupillary distance. In some cases, the pupil determination module 615 may account for various factors that affect the accuracy of the pupillary distance measurement. For instance, the pupil determination module 615 may account for the position of the user's face (when the face is not in a full-frontal view, for example).

Figure 7:
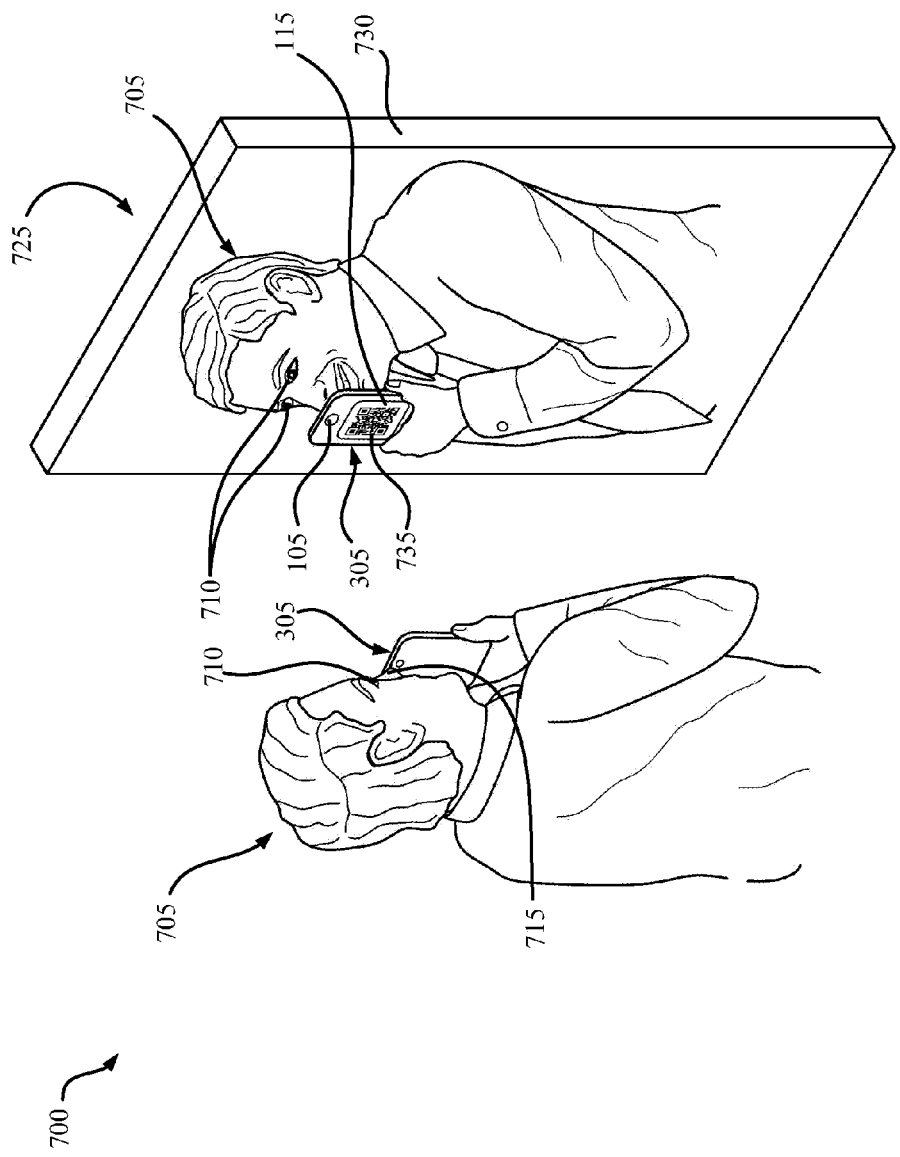
FIG. 7 illustrates an example arrangement for collecting an image of a user using the handheld mobile device to scale the image.

FIG. 7 illustrates an example arrangement 700 for collecting an image of a user 705 using the handheld mobile device 305 to scale the image. The user 705 may hold the handheld mobile device 305 against the nose 715 or other consistent position of the user 705. The user 705 may direct the display 115 of the handheld mobile device 305 and the camera 105 to face toward a mirror 730 so that the display 115 and a QR code 735 displayed by the display 115 are visible in the mirror 730. The user faces directly looking at the mirror 730 so that both eyes 710 and their associated pupils are visible in the mirror 730.

FIG. 7 shows an image 725 (e.g., reflection) of the user 705 and handheld mobile device 305 within the mirror 36. The image 725 includes the user's eyes 710, the handheld mobile device 305, camera 105, display 115, and the device specific QR code 735 being displayed by the display 115. In at least some arrangements, the display 115 shows a window frame that the user can see in the image 725 to make sure that the handheld mobile device 102 and the user's eyes 710 are within the picture being taken by handheld mobile device 305. The user 705 then takes a picture of the image 725.

The handheld mobile device 305 may operate the scaling module 110 to obtain a scale of the picture, or the picture may be sent to a remote location where the scaling module 110 is operating remotely. In a scenario wherein the handheld mobile device 305 operates the scaling module 110, the handheld mobile device 102 may be aware of its make and model and associated dimensions so that the scaling module 110 can scale the image based on the known dimensions of the various features of the handheld mobile device 305. The scaling module 110 may then use the scale of the image to determine the pupillary distance between eyes 710 of the user 30. Alternatively, the scale and image may be transmitted to a different computing device to determine the pupillary distance.

In a scenario where the scaling module 110 is operated remotely, the user may send, with the image, identifying information about the handheld mobile device 305, such as, for example, a make, model, or dimensions. Alternatively, device information will be transmitted via the content of the marker 735. The scale module 110 may then be operated to determine a scale of the image using the identifying information. The scaling module 110 or a different computing device or module may use the scale and image to determine the pupillary distance of the user.

The image collection arrangement of FIG. 7 may be facilitated when the camera 105 is reversible so as to change between taking pictures in a forward or rearward direction relative to a side of the handheld mobile device 305 that includes the display 115. Other types of handheld mobile devices include cameras 105 that are not reversible and take pictures in only a single direction, which is typically a direction facing away from the display 115. In such scenarios, an alternative option is available for obtaining an image of the user holding the handheld mobile device wherein identifying information (a device specific QR code 735, for example) about the handheld mobile device is displayed on the display 115 and is visible in the image collected by camera 105.

Figure 8:
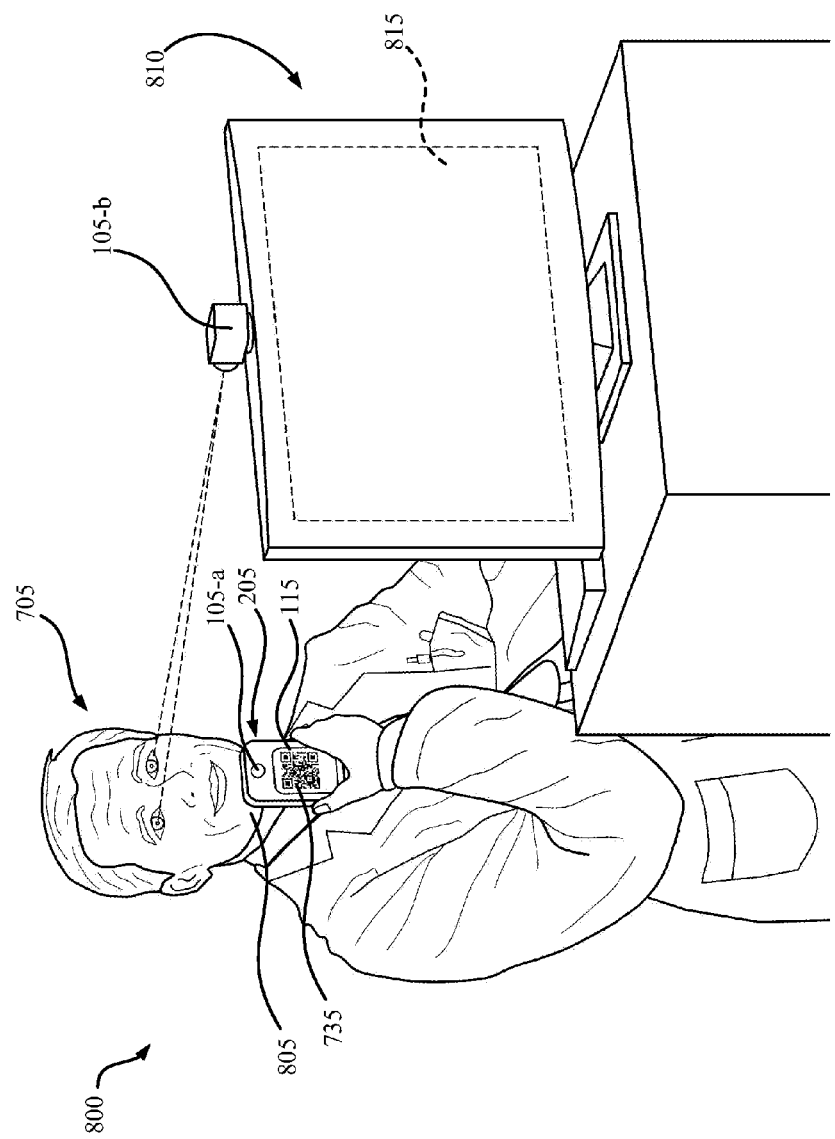
FIG. 8 shows another example arrangement for collecting an image of a user and handheld mobile device.

FIG. 8 shows another example arrangement 800 for collecting an image of a user and handheld mobile device. The user 705 in FIG. 8 is shown holding a handheld mobile device 205 at a predetermined location relative to the user's face (e.g., against the user's chin 805). The display 115 is facing toward a camera 105. Camera 105-*b* is in electronic communication with a computing device 810 that includes a processor. The camera 105-*b* may be mounted separate from computing device 810. Alternatively, as shown in FIG. 8, camera 105-*b* is mounted to computing device 810 in the form of, for example, a web cam attached to a monitor of the computing device 810. Camera 105-*b* may be any second camera in communication with a computing device 810, such as a mobile phone, a tablet computer, a PDA, a laptop, a desktop computer, and the like.

Camera 105-*b* collects an image of user 705 and handheld mobile device 205 (including display 115 and the device specific marker such as a QR code 735 being displayed by the display 115, for example). Computing device 810 may identify handheld mobile device 205 based on the identifying information (e.g., the device specific marker such as a QR code 735) shown on the display 115. Computing device 810 may operate the scaling module 110 to determine a scale of the image collected by the camera 105-*b*. The scale may then be used by scaling module 110 or by another computing device to determine a pupillary distance of the user 705. Alternatively, scaling module 110 may be positioned remote from computing device 810 via communication by a communications network 108 as shown in system 200 of FIG. 2.

As described above, the identifying information displayed on display 115, which is collected by camera 105, may identify at least one of a make, model or dimensions of portions of the handheld mobile device 205 used for scaling purposes. In one example, the handheld mobile device 205 displays a pattern, color scheme, text, numbers or patterns, code, QR code, etc. that are used by computing device 810 (e.g., scaling module 110) to scale the image of the user 705 and handheld mobile device 205 collected by camera 105.

The computing device 810 may be a desktop computer, laptop computer, tablet computer, or other handheld mobile device. In one example, the computing device 810 may be a first handheld mobile device having a camera that is held by one hand of the user, and the handheld mobile device 205 is held against the user, such as the user's chin or forehead by an opposite hand of the user 705. The user operates the first handheld mobile device and/or the handheld mobile device 205 to take a picture of the user 705 and the second handheld mobile device 205.

In one example, the user holds a second handheld mobile device (an iPad, for example) with the screen 815 and front facing camera 105-*b* looking back at the user's face in one hand and the first handheld mobile device 205 (an iPhone, for example) in contact with the user's face (under the user's nose, for example) with the other hand. The user may hold the first handheld mobile device 205 so that the display 115 (e.g., screen) of the device and the front facing camera 105-*a* are looking back at the screen 815 and camera 105-*b* of the second handheld mobile device. In some configurations, this setup may allow the distance between the handheld mobile device and the first handheld mobile device to be determined. In some cases, the determination of this distance may enhance the precision of the scaling and/or of the determination of the pupillary distance by eliminating another variable in the geometric calculations performed by the scaling module 110.

In this configuration, with the first handheld mobile device 205 and the second handheld mobile device facing each other, the first handheld mobile device 205 may view identifying information (e.g., a QR code) on the display 815 of the second handheld mobile device and the second handheld mobile device may view identifying information on the display 115 of the first handheld mobile device. In one example, the distance may be determined based on a known predetermined size of the identifying information. For example, the distance between the devices may be measured based on the difference between an expected size of a QR code and the received size of the QR code. In some cases, the first handheld mobile device and/or the second handheld mobile device may individually and independently determine the distance between the devices. In some cases, the devices may collaborate together to jointly determine the distance between the devices. In some configurations, the two devices may communicate with each other (via the communications network 108, for example). For example, the two devices may communicate with each other in a session initiated by detecting the identifying information on the screen of the other device.

Figure 9:
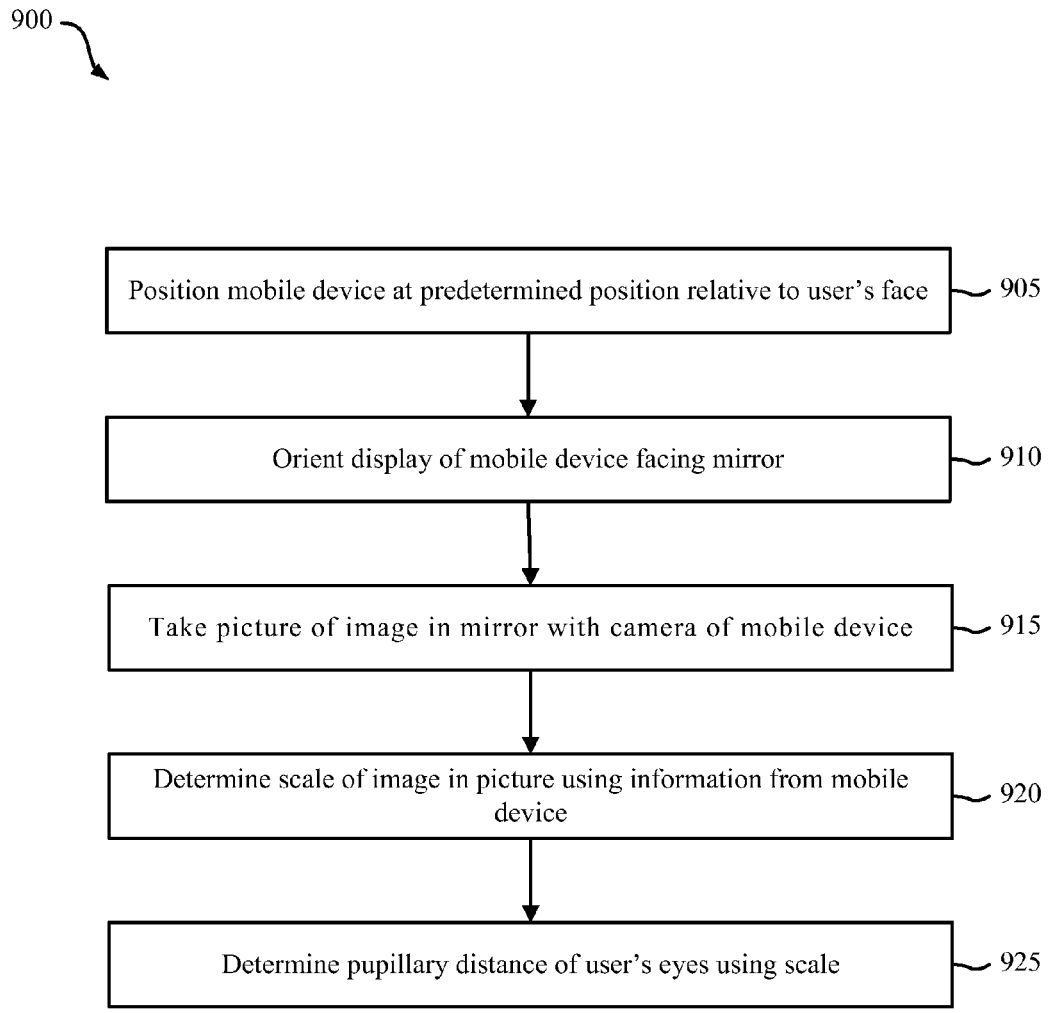
FIGS. 9-12 are flow diagrams showing example methods in accordance with the present disclosure.

Referring now to FIG. 9, an example method 900 in accordance with the present disclosure includes a first operational step 902 of positioning a mobile device at a predetermined position relative to a user's face. The display of the mobile device is oriented facing a mirror in a step 904. A step 906 includes taking a picture of the image in the mirror with a camera of the mobile device. A step 908 includes determining a scale of the image and the picture using information from the mobile device. As noted above, the information from the mobile device may include, but is in no way limited to, the features of the mobile device itself; a code, image, color, shape, letters, etc. displayed on the display of the mobile device, and the like. A step 910 includes determining a pupillary distance of the user's eyes using the scale determined in step 908.

Figure 10:
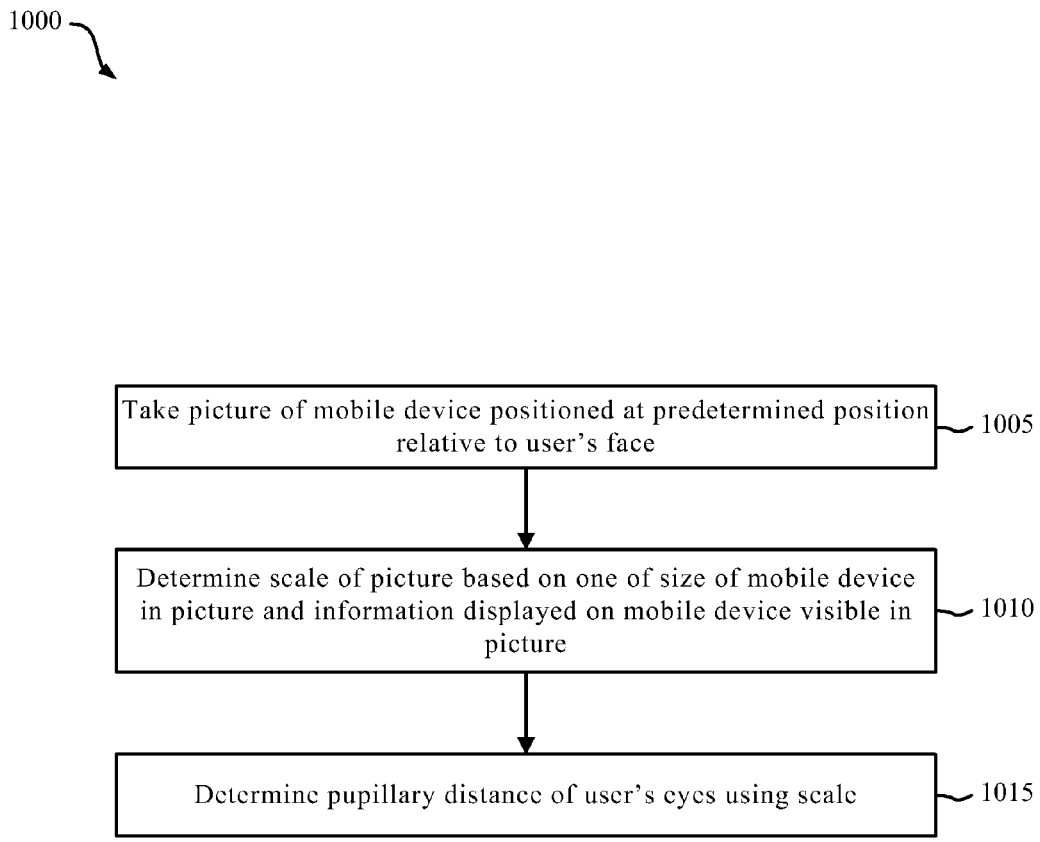

FIG. 10 shows another method 1000 that includes a first operational step 1002 of taking a picture of a mobile device positioned at a predetermined position relative to a user's face. Method 1000 also includes determining a scale of the picture based on one of a size of the mobile device in the picture and information displayed on a display of the mobile device visible in the picture in a step 1004. A step 1006 includes determining a pupillary distance of the user's eyes using the scale determined in step 1004.

Figure 11:
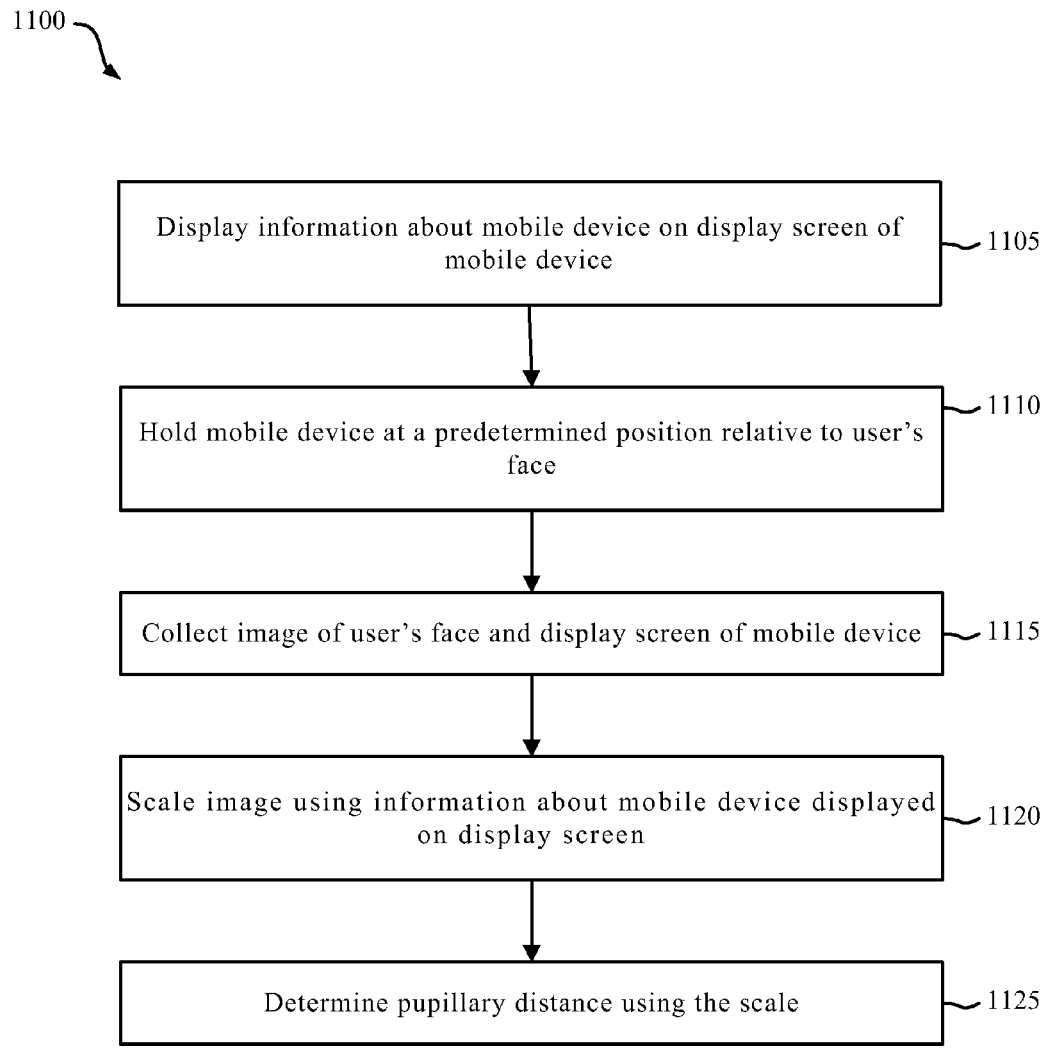

FIG. 11 shows another example method 1100 that includes a first operational step of displaying information about a mobile device on a display screen of the mobile device in a step 1102. A step 1104 includes holding a mobile device at a predetermined position relative to a user's face. An image of the user's face and a display screen of the mobile device are collected in a step 1106. A step 1108 includes scaling the image using identifying information about the mobile device displayed on the display screen. A step 1110 includes determining a pupillary distance using the scale determined in step 1108.

Figure 12:
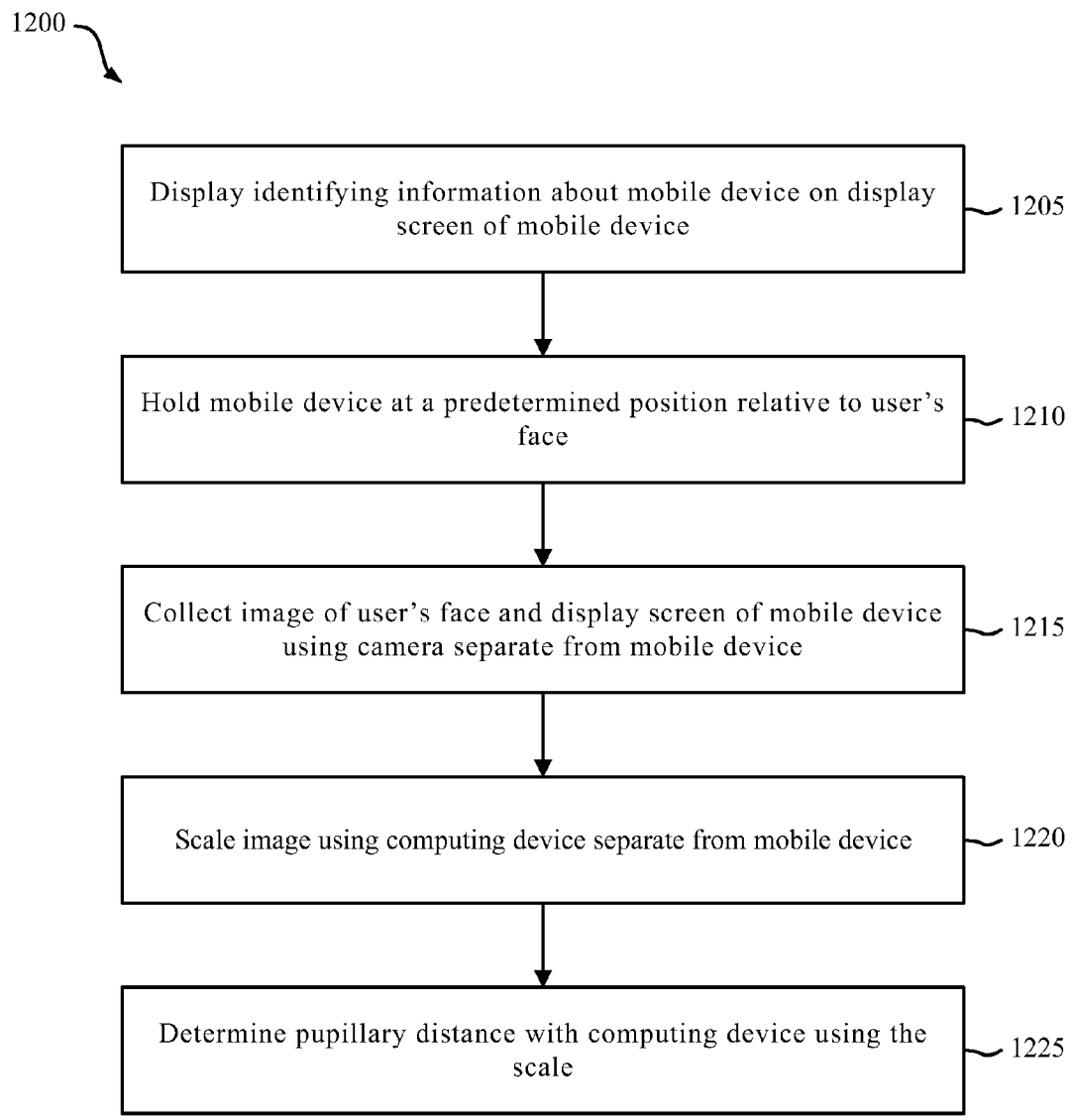

FIG. 12 shows a method 1200 that includes a step 1202 of displaying identifying information about a mobile device on a display screen of the mobile device. Step 1204 includes holding the mobile device at a predetermined position relative to a user's face. An image of the user's face and the display screen of the mobile device are collected using a camera separate from the mobile device in a step 1206. The image is scaled using a computing device separate from the mobile device in a step 1208. A step 1210 includes determining a pupillary distance with the computing device using the scale.

Figure 13:
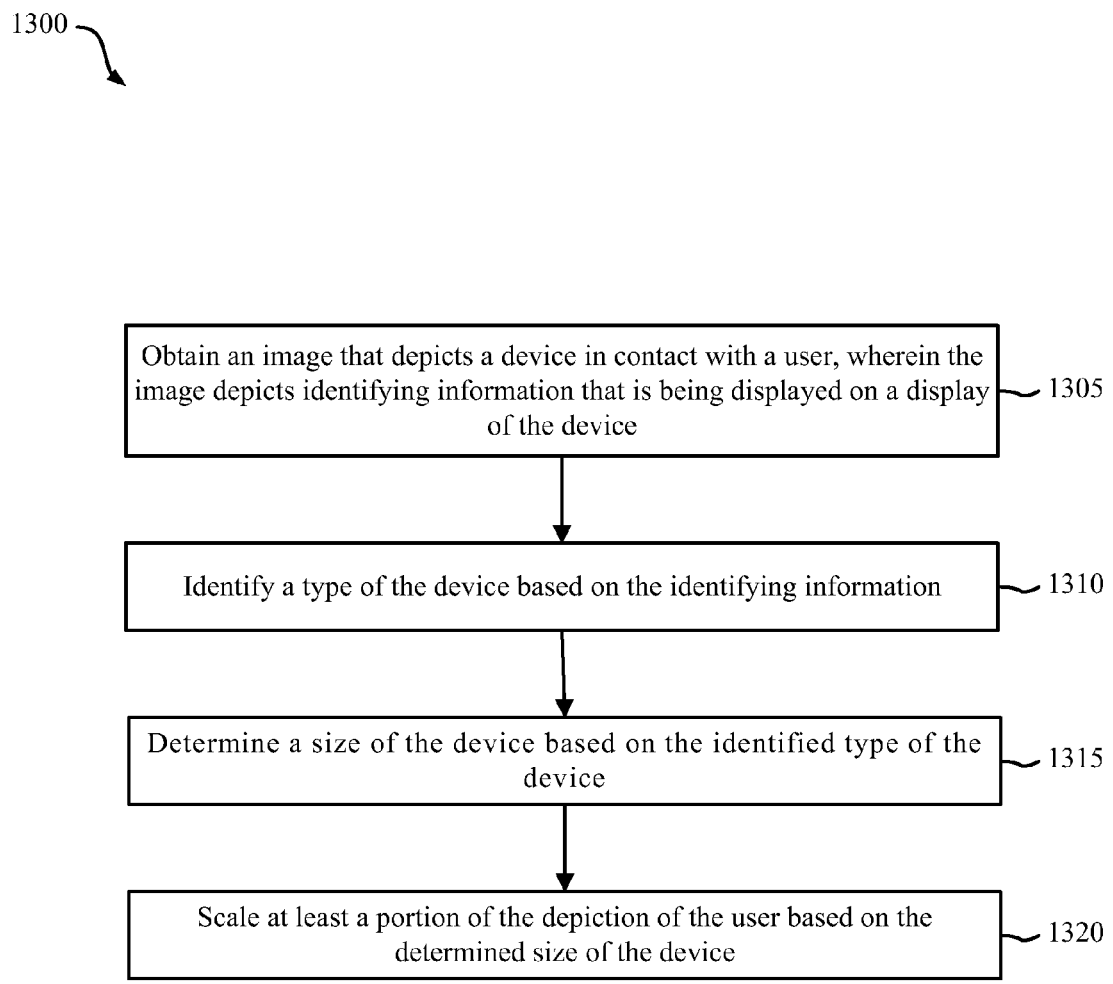
FIG. 13 is a flow diagram illustrating one embodiment of a method to scale an image.

FIG. 13 is a flow diagram illustrating one embodiment of a method 1300 to scale an image. In one configuration, the method 1300 may be implemented by a device such as computing device 205 and/or mobile device 305 illustrated in FIG. 2 or 3. In particular, the method 1300 may be implemented by the scaling module 110 of FIG. 1, 2, 3, or 4.

At block 1305, an image that depicts a device in contact with a user may be obtained. The image may depict identifying information that is being displayed on a display of the device. In one example, the image may be obtained by a camera that is coupled to the device. In another example, the image may be obtained by a camera that is coupled to a second device. In yet another example, the image may be obtained from a storage medium. In one example, the depiction of the device in contact with the user may correspond to the arrangements described with reference to FIGS. 7 and/or 8.

At block 1310, a type of device may be identified based on the identifying information. For example, the identifying information may indicate the make and model of the device. In another example, the identifying information may indicate one or more dimensions of the device. In some configurations, the identifying information may be provided in the form of a Quick Response (QR) code.

At block 1315, a size of the device may be determined based on the identified type of the device. For example (in the case that the identifying information indicates a make and model, for instance), the physical dimensions (e.g., size) of the device may be determined based on the identified make and model of the device. In another example (in the case that the identifying information indicates a dimension of the device, for instance), the one or more identified dimensions of the device may directly be used as the physical dimensions of the device.

At block 1320, at least a portion of the depiction of the user may be scaled based on the determined size of the device. For example, the depiction of the user may be scaled based on a relationship between the depiction of the device and the depiction of the user and the known size of the device.

Figure 14:
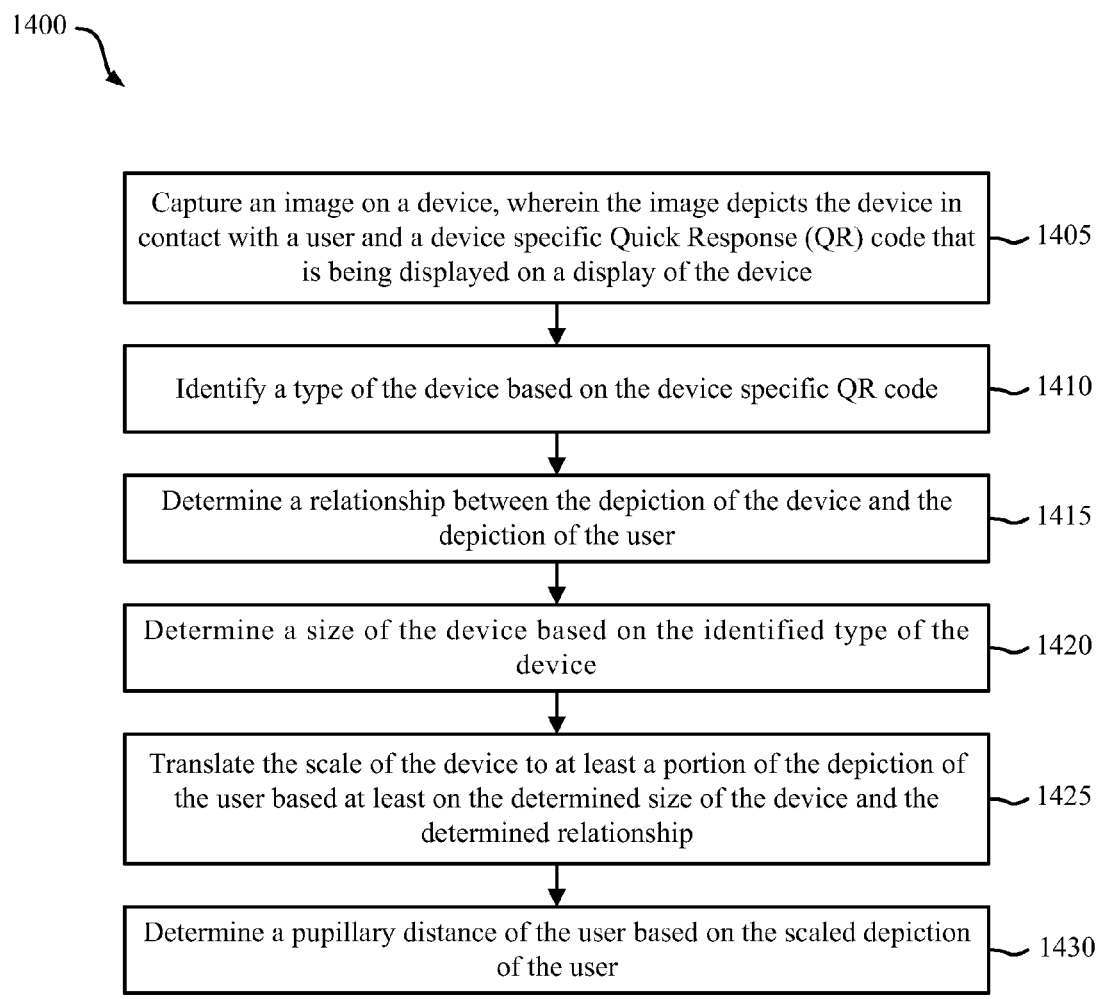
FIG. 14 is a flow diagram illustrating another embodiment of a method to scale an image.

FIG. 14 is a flow diagram illustrating another embodiment of a method 1400 to scale an image. In one configuration, the method 1400 may be implemented by a device such as computing device 205 and/or mobile device 305 illustrated in FIG. 2 or 3. In particular, the method 1400 may be implemented by the scaling module 110 of FIG. 1, 2, 3, or 4.

At block 1405, an image may be captured on a device. The image may depict the device in contact with a user and a device specific Quick Response (QR) code that is being displayed on a display of the device. In some configurations, the device specific QR code may be formatted so that the QR code itself may have a predetermined size. In some cases, this may allow the QR code to be used to scale the device, the user, and/or any other objects depicted in the image. Additionally or alternatively, the predetermined size of the QR code may be used to determine the distance between the camera that is capturing the device and the image that is being captured by the camera (the reflection in the mirror, for example).

At block 1410, a type of device may be identified based on the device specific QR code. For example, the device specific QR code may indicate the make and model of the device and/or the physical dimensions of the device. The appropriate QR code may be downloaded to the device via a web browser or other application having access to the communications network 108.

At block 1415, a relationship between the depiction of the device and the depiction of the user may be determined. For example, the relationship may be a relationship of relative sizes of the depiction of the device and the depiction of the user. It may be noted that the contact between the device and the user may allow for accurate relationships to be determined between the relative sizes of the depiction of the device and the depiction of the user. In some cases, the relationship may include one or more adjustments to account for difference in depth between the device and various features of the user. In one example, these differences may be based on averages (the average difference in depth between the depth of the eyes and the depth of the chin, and/or the average difference in depth between the depth of the eyes and the tip of the nose). In some cases, properly determining the relationship between the depiction of the device and the depiction of the user may enhance the accuracy of the scaling (and the pupillary distance measurement, for example).

At block 1420, a size of the device may be determined based on the identified type of the device. At block 1425, the scale of the depiction of the device may be translated to at least a portion of the depiction of the user based on the determined size of the device and the determined relationship. For example, the translation may involve accounting for the difference in depth based on an average difference in depth between facial features. At block 1430, a pupillary distance of the user may be determined based on the scaled depiction of the user.

Any of these steps of any of the example methods shown in FIGS. 9-14 may be interchanged, added to, or removed from in alternative embodiments. The methods of FIGS. 9-14 are merely exemplary and may represent at least in part some of the functionality of the systems 100, 200 described above with reference to FIGS. 1-2 and the arrangements described with reference to FIGS. 7 and 8.

Figure 15:
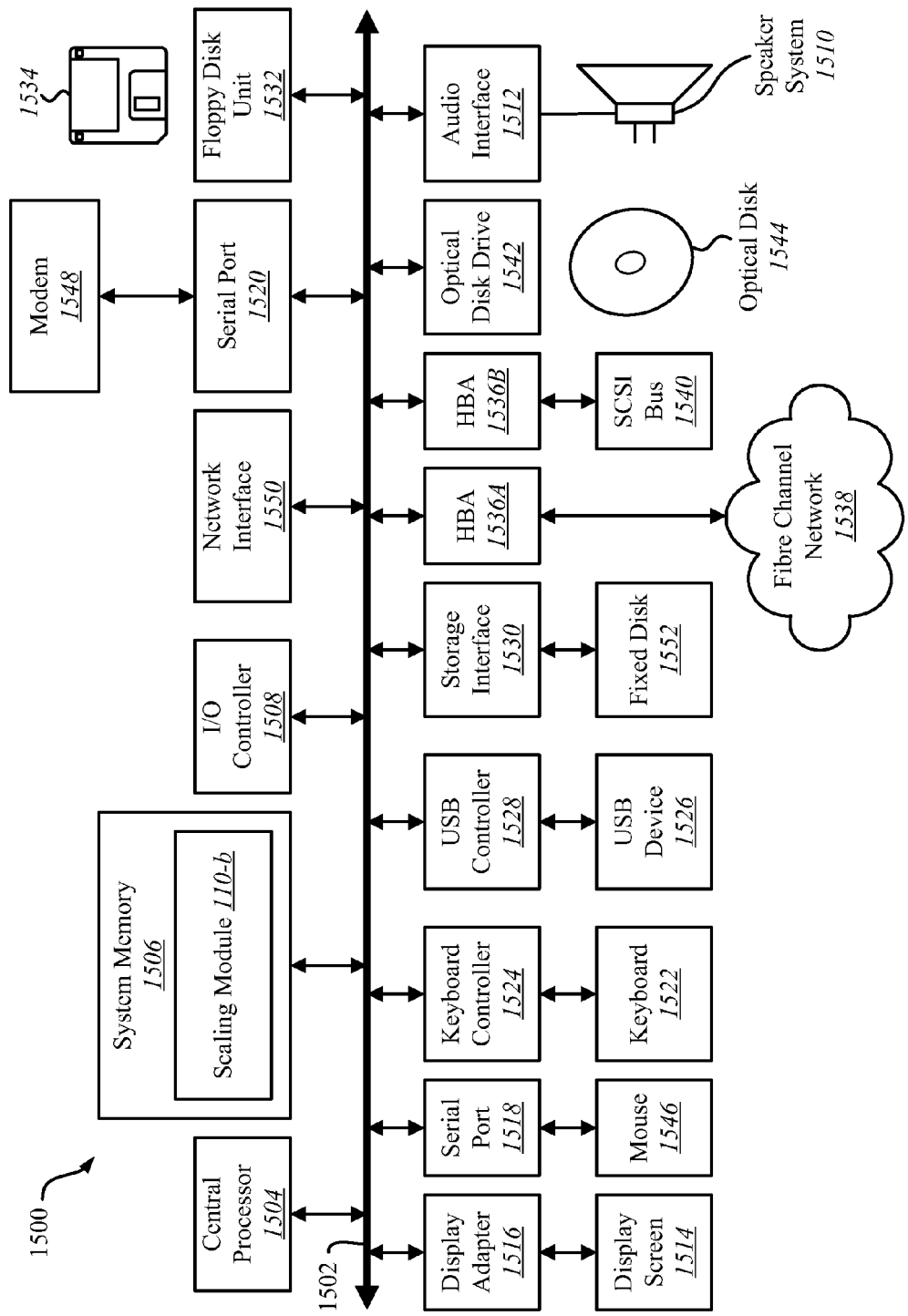
FIG. 15 depicts a block diagram of a computer system suitable for implementing the present systems and methods.

FIG. 15 depicts a block diagram of a computer system 1500 suitable for implementing the present systems and methods. Computer system 1500 includes a bus 1512 which interconnects major subsystems of computer system 1510, such as a central processor 1514, a system memory 1517 (typically RAM, but which may also include ROM, flash RAM, or the like), an input/output controller 1518, an external audio device, such as a speaker system 1520 via an audio output interface 1522, an external device, such as a display screen 1524 via display adapter 1526, serial ports 1528 and 1530, a keyboard 1532 (interfaced with a keyboard controller 1533), multiple USB devices 1592 (interfaced with a USB controller 1591), a storage interface 1534, a floppy disk unit 1537 operative to receive a floppy disk 1538, a host bus adapter (HBA) interface card 1535A operative to connect with a Fibre Channel network 1590, a host bus adapter (HBA) interface card 1535B operative to connect to a SCSI bus 1539, and an optical disk drive 1540 operative to receive an optical disk 1542. Also included are a mouse 1546 (or other point-and-click device, coupled to bus 1512 via serial port 1528), a modem 1547 (coupled to bus 1512 via serial port 1530), and a network interface 1548 (coupled directly to bus 1512).

Bus 1512 allows data communication between central processor 1514 and system memory 1517, which may include read-only memory (ROM) or flash memory (neither shown), and random access memory (RAM) (not shown), as previously noted. The RAM is generally the main memory into which the operating system and application programs are loaded. The ROM or flash memory can contain, among other code, the Basic Input-Output system (BIOS) which controls basic hardware operation such as the interaction with peripheral components or devices. For example, a scaling module 110-b to implement the present systems and methods may be stored within the system memory 1517. The scaling module 110-b may be an example of the scaling module 110 illustrated in FIG. 1, 2, 3, or 4. Applications resident with computer system 1500 are generally stored on and accessed via a non-transitory computer readable medium, such as a hard disk drive (e.g., fixed disk 1544), an optical drive (e.g., optical drive 1540), a floppy disk unit 1537, or other storage medium. Additionally, applications can be in the form of electronic signals modulated in accordance with the application and data communication technology when accessed via network modem 1547 or interface 1548.

Storage interface 1534, as with the other storage interfaces of computer system 1500, can connect to a standard computer readable medium for storage and/or retrieval of information, such as a fixed disk drive 1544. Fixed disk drive 1544 may be a part of computer system 1500 or may be separate and accessed through other interface systems. Modem 1547 may provide a direct connection to a remote server via a telephone link or to the Internet via an internet service provider (ISP). Network interface 1548 may provide a direct connection to a remote server via a direct network link to the Internet via a POP (point of presence). Network interface 1548 may provide such connection using wireless techniques, including digital cellular telephone connection, Cellular Digital Packet Data (CDPD) connection, digital satellite data connection, or the like.

Many other devices or subsystems (not shown) may be connected in a similar manner (e.g., document scanners, digital cameras, and so on). Conversely, all of the devices shown in FIG. 15 need not be present to practice the present systems and methods. The devices and subsystems can be interconnected in different ways from that shown in FIG. 15. The operation of a computer system such as that shown in FIG. 15 is readily known in the art and is not discussed in detail in this application. Code to implement the present disclosure can be stored in a non-transitory computer-readable medium such as one or more of system memory 1517, fixed disk 1544, optical disk 1542, or floppy disk 1538. The operating system provided on computer system 1500 may be MS-DOS®, MS-WINDOWS®, OS/2®, UNIX®, Linux®, or another known operating system.

Moreover, regarding the signals described herein, those skilled in the art will recognize that a signal can be directly transmitted from a first block to a second block, or a signal can be modified (e.g., amplified, attenuated, delayed, latched, buffered, inverted, filtered, or otherwise modified) between the blocks. Although the signals of the above described embodiment are characterized as transmitted from one block to the next, other embodiments of the present systems and methods may include modified signals in place of such directly transmitted signals as long as the informational and/or functional aspect of the signal is transmitted between blocks. To some extent, a signal input at a second block can be conceptualized as a second signal derived from a first signal output from a first block due to physical limitations of the circuitry involved (e.g., there will inevitably be some attenuation and delay). Therefore, as used herein, a second signal derived from a first signal includes the first signal or any modifications to the first signal, whether due to circuit limitations or due to passage through other circuit elements which do not change the informational and/or final functional aspect of the first signal.

Figure 16:
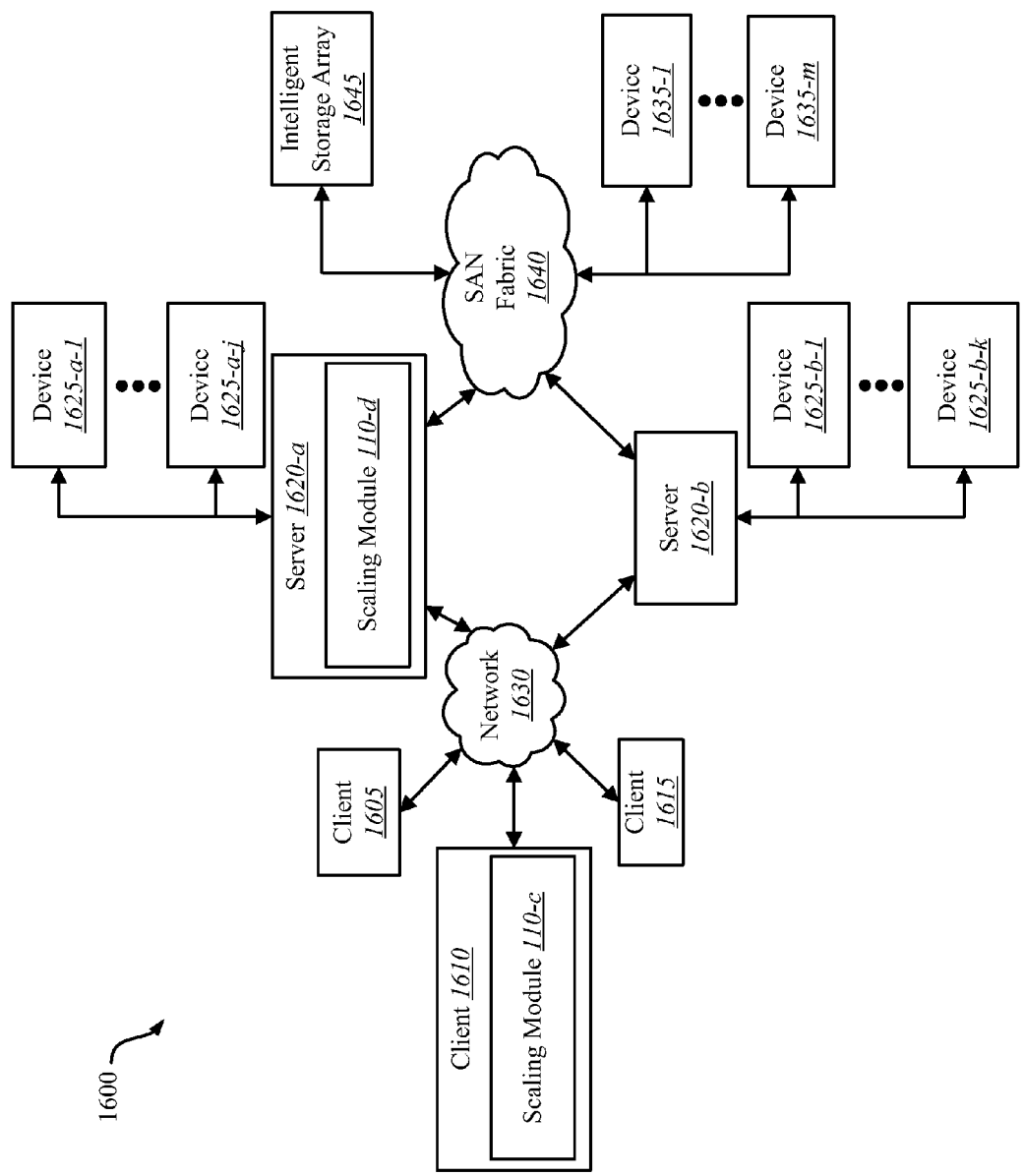
FIG. 16 is a block diagram depicting a network architecture in which client systems, as well as storage servers (any of which can be implemented using computer system), are coupled to a network.

FIG. 16 is a block diagram depicting an exemplary network architecture 1600 in which client systems 1605, 1610 and 1615, as well as storage servers 1625A, 1625B (any of which can be implemented using computer system 1000), are coupled to a network 1620. In one embodiment, the scaling module 110-c, 110-d may be located within the storage servers 1625A, 1625B and/or the client systems 1605, 1610, 1615 to implement the present systems and methods. The storage server 1625A is further depicted as having storage devices 1630A(1)-(N) directly attached, and storage server 1625B is depicted with storage devices 1630B(1)-(N) directly attached. SAN fabric 1635 supports access to storage devices 1645(1)-(N) by storage servers 1625A, 1625B, and so by client systems 1605, 1610, 1615 via network 1620. Intelligent storage array 1640 is also shown as an example of a specific storage device accessible via SAN fabric 1635.

With reference to computer system 1500, modem 1547, network interface 1548, or some other method can be used to provide connectivity from each of client computer systems 1605, 1610, and 1615 to network 1620. Client systems 1605, 1610, and 1615 are able to access information on storage server 1625A or 1625B using, for example, a web browser, or other client software (not shown). Such a client allows client systems 1605, 1610, and 1615 to access data hosted by storage server 1625A or 1625B or one of storage devices 1630A(1)-(N), 1630B(1)-(N), 1645(1)-(N) or intelligent storage array 1640. FIG. 16 depicts the use of a network such as the Internet for exchanging data, but the present systems and methods are not limited to the Internet or any particular network-based environment.

While the foregoing disclosure sets forth various embodiments using specific block diagrams, flowcharts, and examples, each block diagram component, flowchart step, operation, and/or component described and/or illustrated herein may be implemented, individually and/or collectively, using a wide range of hardware, software, or firmware (or any combination thereof) configurations. In addition, any disclosure of components contained within other components should be considered exemplary in nature since many other architectures can be implemented to achieve the same functionality.

The process parameters and sequence of steps described and/or illustrated herein are given by way of example only and can be varied as desired. For example, while the steps illustrated and/or described herein may be shown or discussed in a particular order, these steps do not necessarily need to be performed in the order illustrated or discussed. The various exemplary methods described and/or illustrated herein may also omit one or more of the steps described or illustrated herein or include additional steps in addition to those disclosed.

Furthermore, while various embodiments have been described and/or illustrated herein in the context of fully functional computing systems, one or more of these exemplary embodiments may be distributed as a program product in a variety of forms, regardless of the particular type of computer-readable media used to actually carry out the distribution. The embodiments disclosed herein may also be implemented using software modules that perform certain tasks. These software modules may include script, batch, or other executable files that may be stored on a computer-readable storage medium or in a computing system. In some embodiments, these software modules may configure a computing system to perform one or more of the exemplary embodiments disclosed herein.

The foregoing description, for purpose of explanation, has been described with reference to specific embodiments. However, the illustrative discussions above are not intended to be exhaustive or to limit the invention to the precise forms disclosed. Many modifications and variations are possible in view of the above teachings. The embodiments were chosen and described in order to best explain the principles of the present systems and methods and their practical applications, to thereby enable others skilled in the art to best utilize the present systems and methods and various embodiments with various modifications as may be suited to the particular use contemplated.

Unless otherwise noted, the terms "a" or "an," as used in the specification and claims, are to be construed as meaning "at least one of." In addition, for ease of use, the words "including" and "having," as used in the specification and claims, are interchangeable with and have the same meaning as the word "comprising."

I claim:

1. A computer-implemented method for scaling an image, comprising:
    obtaining, by a processor of a device, an image of a reflection that depicts the device in contact with a face of a user, wherein the image depicts a display of the device displaying a Quick Response (QR) code; and
    scaling, by the processor, at least a portion of the depiction of the user based on the captured reflection including the QR code displayed on the device.

2. The method of claim 1, wherein the image is captured by the device.

3. The method of claim 1, wherein the QR code includes identifying information, the identifying information comprising one or more of a make of the device, a model of the device, and dimensions of the device, wherein at least a portion of the depiction of the user is scaled based on the determined size of the device.

4. The method of claim 3, further comprising:
    identifying, by the processor, a type of the device based on the identifying information; and
    determining, by the processor, a size of the device based on the identified type of the device.

5. The method of claim 1, further comprising determining a relationship between the depiction of the device and the depiction of the user.

6. The method of claim 5, wherein scaling the at least a portion of the depiction of the user comprises translating the scale of the device to the at least a portion of the depiction of the user based on the determined relationship.

7. The method of claim 1, wherein the identifying information has a predetermined size, and wherein one or more of the depiction of the device and the at least a portion of the depiction of the user is scaled based on the predetermined size.

8. The method of claim 7, further comprising determining a distance between the device and a second device that is capturing the image.

9. The method of claim 1, wherein the image is captured by a front-facing camera of the device.

10. A device configured to scale an image, comprising:
    a processor; and
    memory in electronic communication with the processor; and
    instructions stored in the memory, the instructions being executable by the processor to:
        obtain an image of a reflection that depicts the device in contact with a face of a user, wherein the image depicts a display of the device displaying a Quick Response (QR) code; and
        scale at least a portion of the depiction of the user based on the captured reflection including the QR code displayed on the device.

11. The device of claim 10, wherein the image is captured by the device.

12. The device of claim 10, wherein the QR code includes identifying information, the identifying information comprising one or more of a make, a model, and a dimension of the device, wherein at least a portion of the depiction of the user is scaled based on the determined size of the device.

13. The device of claim 10, wherein the instructions are further executable by the processor to determine a relationship between the depiction of the device and the depiction of the user.

14. The device of claim 13, wherein the instructions to scale the at least a portion of the depiction of the user are further executable by the processor to translate the scale of the device to the at least a portion of the depiction of the user based on the determined relationship.

15. The device of claim 10, wherein the identifying information has a predetermined size, and wherein one or more of the depiction of the device and the at least a portion of the depiction of the user is scaled based on the predetermined size.

16. The device of claim 15, wherein the instructions are further executable by the processor to determine a distance between the device and a second device that is capturing the image.

17. A computer-program product to scale an image, the computer-program product comprising a non-transitory computer-readable medium having instructions thereon, the instructions being executable by a processor of a device to:
    obtain an image of a reflection that depicts the device in contact with a face of a user, wherein the image depicts a display of the device displaying a Quick Response (QR) code;
    scale at least a portion of the depiction of the user based on the captured reflection including the QR code displayed on the device.

18. A computer-implemented method for scaling an image, comprising:
    obtaining, by a processor, an image that depicts a device in relation to a face of a user, wherein the image depicts identifying information that is being displayed on a display of the device, the identifying information comprising a Quick Response (QR) code; and
    determining, by the processor, a pupillary distance of the user based on the scaled depiction of the user based on the QR code displayed on the device.

19. The method of claim 18, wherein the image is captured by the device.

20. The method of claim 18, wherein the QR code includes identifying information, the identifying information comprising one or more of a make of the device, a model of the device, and dimensions of the device, wherein at least a portion of the depiction of the pupillary distance of the user is determined based on the determined size of the device.

* * * * *